United States Patent
Lindfors et al.

(10) Patent No.: US 11,458,106 B2
(45) Date of Patent: Oct. 4, 2022

(54) LIPID NANOPARTICLES COMPRISING LIPOPHILIC ANTI-INFLAMMATORY AGENTS AND METHODS OF USE THEREOF

(71) Applicant: ASTRAZENECA AB, Södertälje (SE)

(72) Inventors: Lennart Lindfors, Mölndal (SE); Tomas Kjellman, Mölndal (SE)

(73) Assignee: ASTRAZENECA AB, Södertälje (SE)

( * ) Notice: Subject to any disclaimer, the term of this patent is extended or adjusted under 35 U.S.C. 154(b) by 82 days.

(21) Appl. No.: 15/589,181

(22) Filed: May 8, 2017

(65) Prior Publication Data

US 2017/0367988 A1 Dec. 28, 2017

Related U.S. Application Data

(60) Provisional application No. 62/449,623, filed on Jan. 24, 2017, provisional application No. 62/359,429, (Continued)

(51) Int. Cl.
*A61K 9/127* (2006.01)
*A61K 9/51* (2006.01)
(Continued)

(52) U.S. Cl.
CPC .......... *A61K 9/5123* (2013.01); *A61K 9/1075* (2013.01); *A61K 9/1272* (2013.01);
(Continued)

(58) Field of Classification Search
None
See application file for complete search history.

(56) References Cited

U.S. PATENT DOCUMENTS 6,045,828 A * 4/2000 Bystrom .............. A61K 9/0075
424/489
2006/0062841 A1 3/2006 Huang et al.
(Continued)

FOREIGN PATENT DOCUMENTS

CN 101708338 A 5/2010
CN 104873464 A 9/2015
(Continued)

OTHER PUBLICATIONS

Tan, Y., et al. Human Gene Therapy (1999), 10(13); 2153-2161.*
(Continued)

*Primary Examiner* — Kevin S Orwig

(57) ABSTRACT

The immunostimulatory effect of lipid nanoparticles (LNPs) continues to block their use for safe and effective delivery of pharmaceutical drugs. Consequently, there exists a need to develop effective LNP delivery systems with an increased therapeutic window that do not trigger an inflammatory response. Disclosed herein are lipid nanoparticles comprising a lipid phase and at least one lipophilic anti-inflammatory agent, and pharmaceutical compositions comprising lipid nanoparticles and methods for using lipid nanoparticles. The anti-inflammatory lipid nanoparticles disclosed herein may further serve as platforms for selective delivery of, for example, nucleic acid segments to target cells and tissues, such as antisense oligonucleotides, DNA, mRNAs, siRNAs, Cas9-guideRNA complex.

8 Claims, 15 Drawing Sheets

Rofleponide Calc LogP=2.6

R-C5 Calc LogP=5.3

R-C14 Calc LogP=10.1

R-C16 Calc LogP=11.1

R-C18: Calc LogP=12.2

Related U.S. Application Data filed on Jul. 7, 2016, provisional application No. 62/333,574, filed on May 9, 2016.

(51) Int. Cl.
  *A61K 45/06* (2006.01)
  *C12N 15/88* (2006.01)
  *A61K 9/107* (2006.01)
  *A61K 31/58* (2006.01)
  *A61K 31/7088* (2006.01)

(52) U.S. Cl.
  CPC ............ *A61K 9/5146* (2013.01); *A61K 31/58* (2013.01); *A61K 31/7088* (2013.01); *A61K 45/06* (2013.01); *C12N 15/88* (2013.01)

(56) References Cited

U.S. PATENT DOCUMENTS

2010/0324120 A1* 12/2010 Chen .................... A61K 9/1272
                                                514/44 A
2013/0156849 A1   6/2013 de Fougerolles et al.

FOREIGN PATENT DOCUMENTS

| | | |
|---|---|---|
| CN | 105283175 A | 1/2016 |
| CN | 105338979 A | 2/2016 |
| EP | 2638896 A1 | 9/2013 |
| WO | 2010/144740 A1 | 12/2010 |
| WO | WO 2012/127037 A2 | 9/2012 |
| WO | 2014/179762 A1 | 11/2014 |
| WO | 2014/179773 A2 | 11/2014 |
| WO | WO 2017/194454 A1 | 11/2017 |

OTHER PUBLICATIONS

Abrams, et al., "Evaluation of efficacy, biodistribution, and inflammation for a potent siRNA nanoparticle: effect of dexamethasone co-treatment", Mol Ther. Jan. 2010, (1): 171-80.

International Search Report for PCT/EP2017/060891, dated Jul. 14, 2017.

C. Ahlström-Emanuelsson, "Topical treatment with aqueous solutions of rofleponide palmitate and budesonide in a pollen-season model of allergic rhinitis", Clin Exp Allergy 2004; 34:731-735.

* cited by examiner

Rofleponide  Calc LogP=2.6 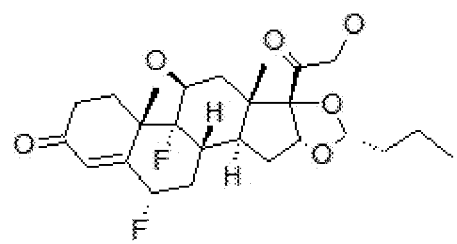
R-C5  Calc LogP=5.3 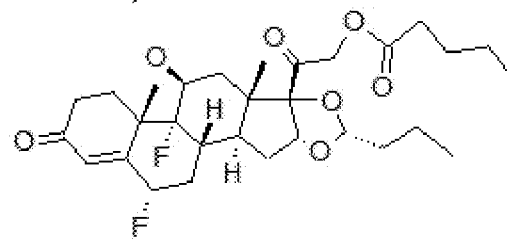
R-C14 Calc LogP=10.1 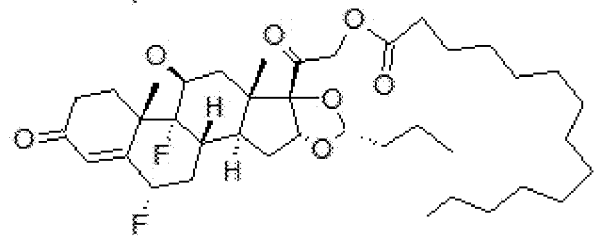
R-C16 Calc LogP=11.1 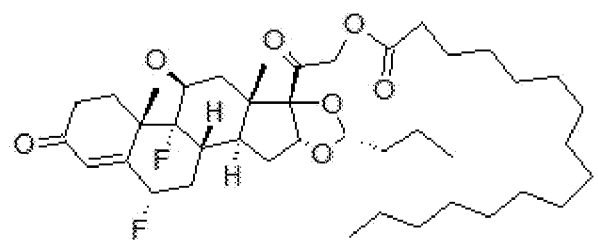
R-C18: Calc LogP=12.2 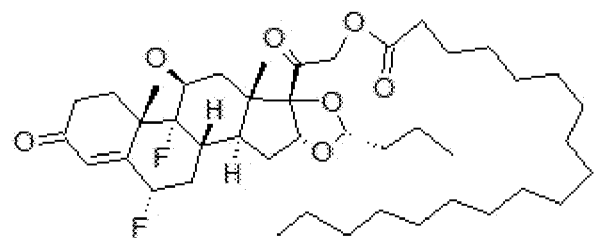
FIG. 1B

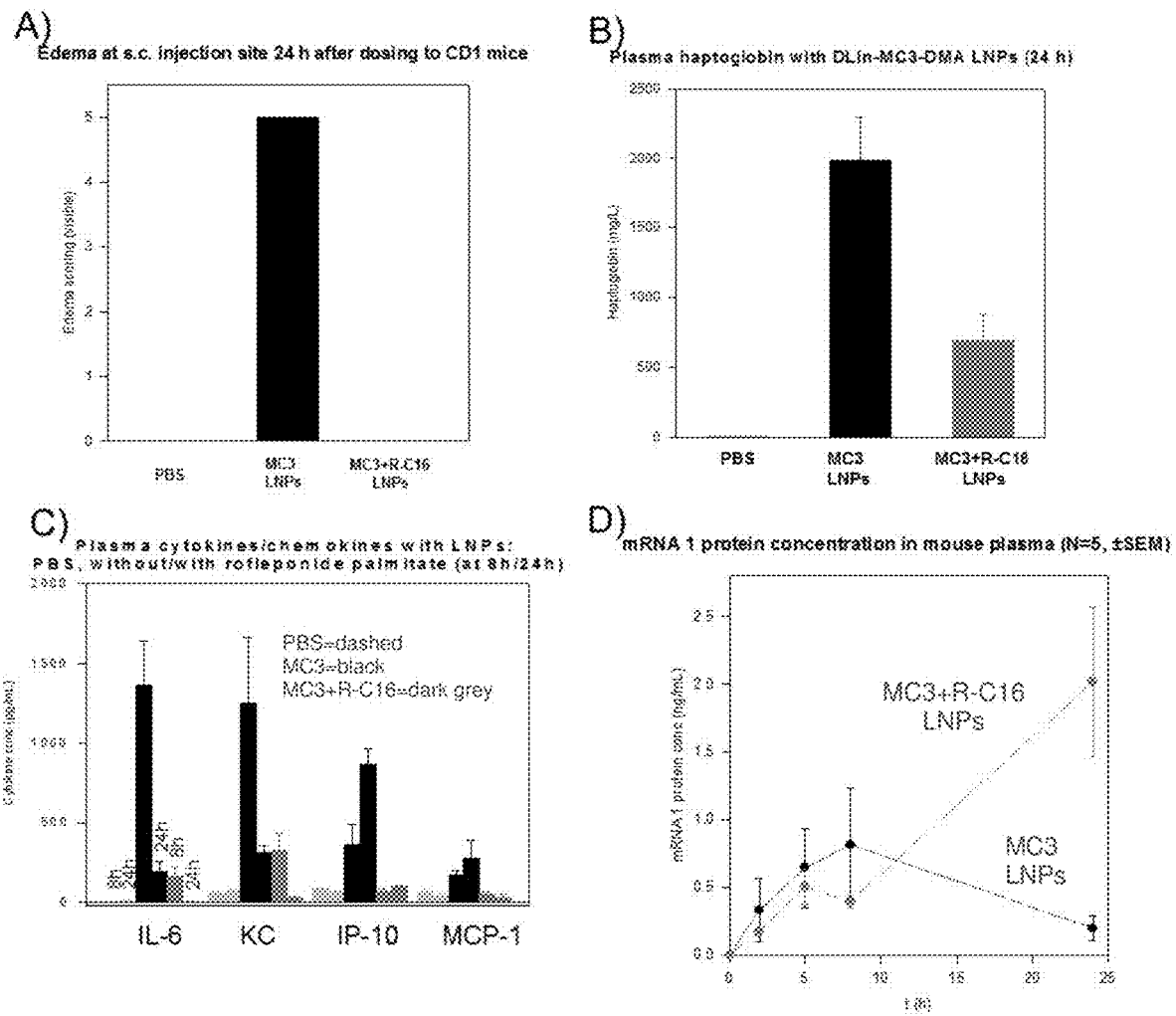
FIGS. 2A-D

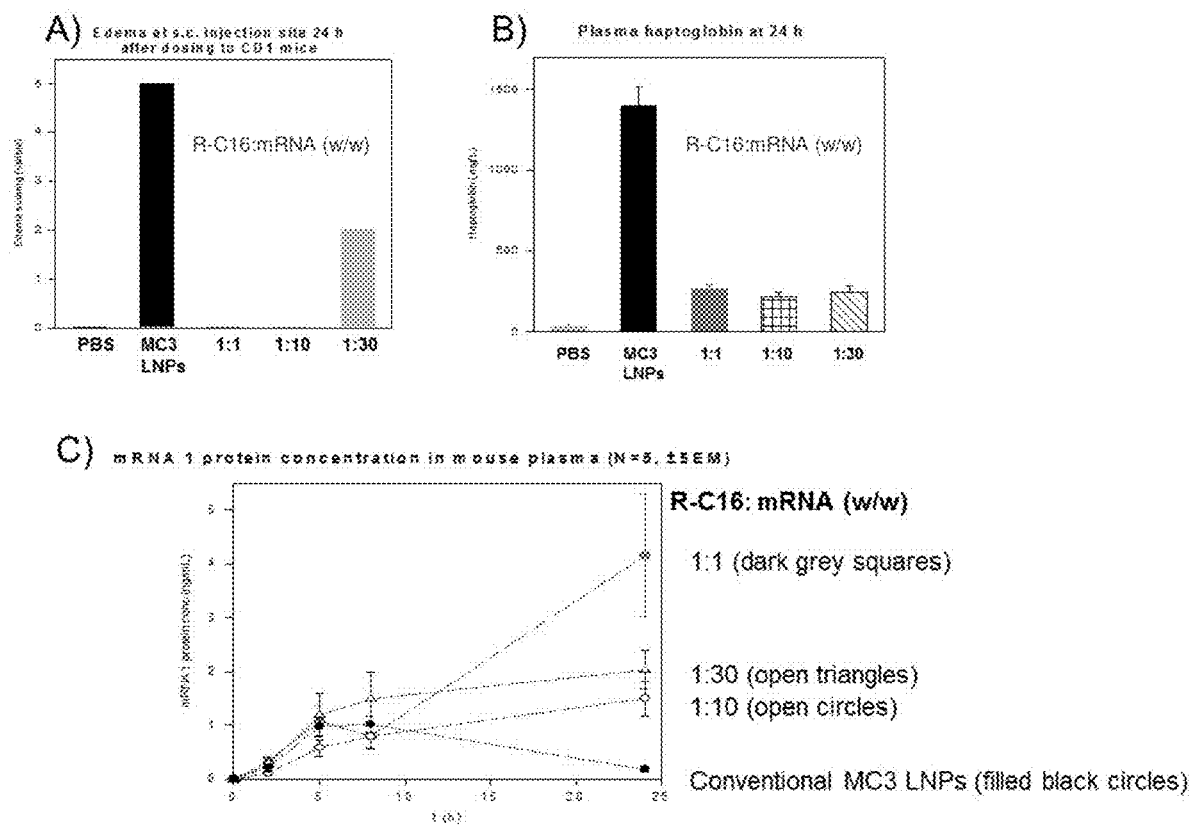
FIGS. 3A-C

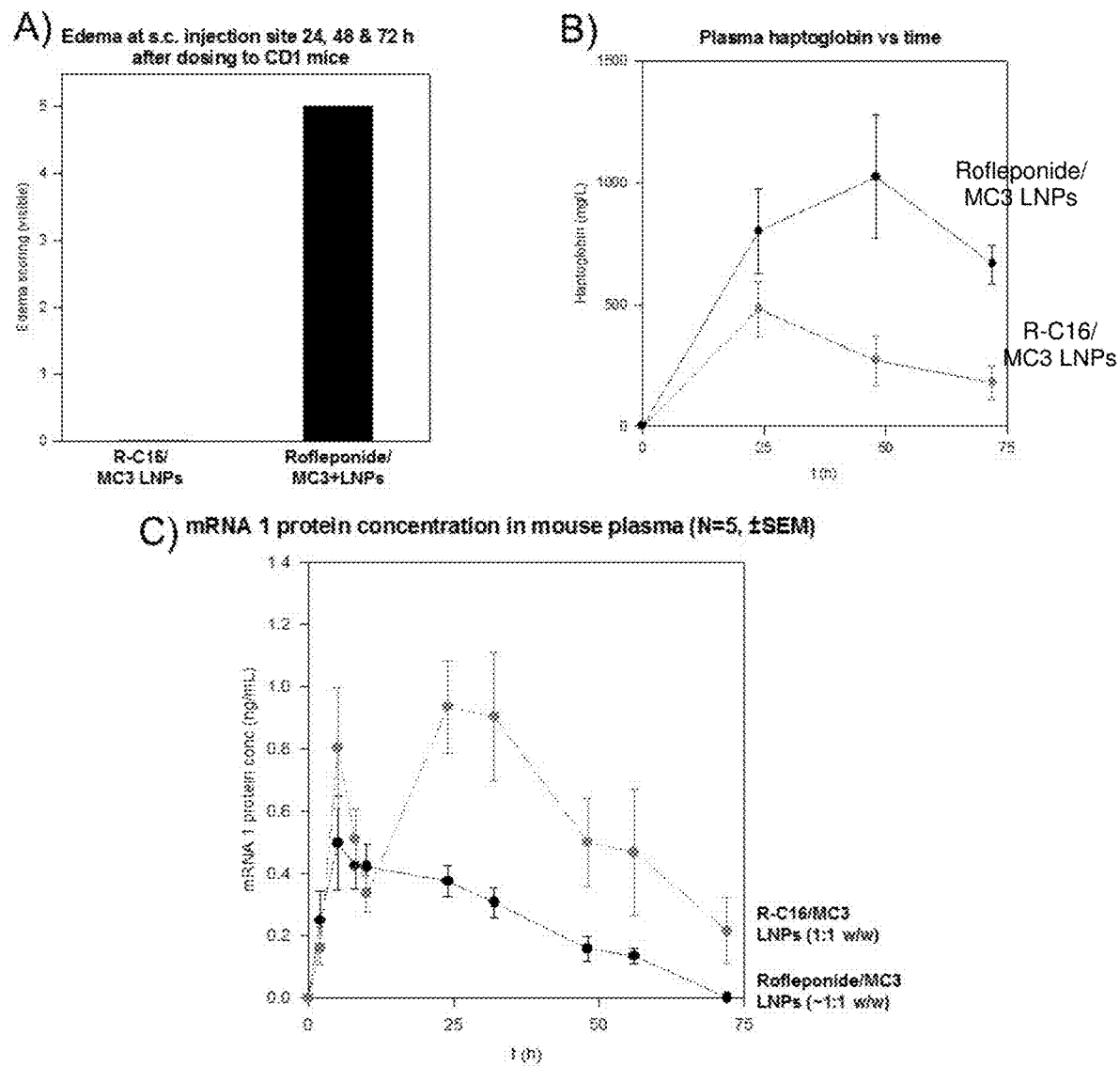
FIGS.4A-C

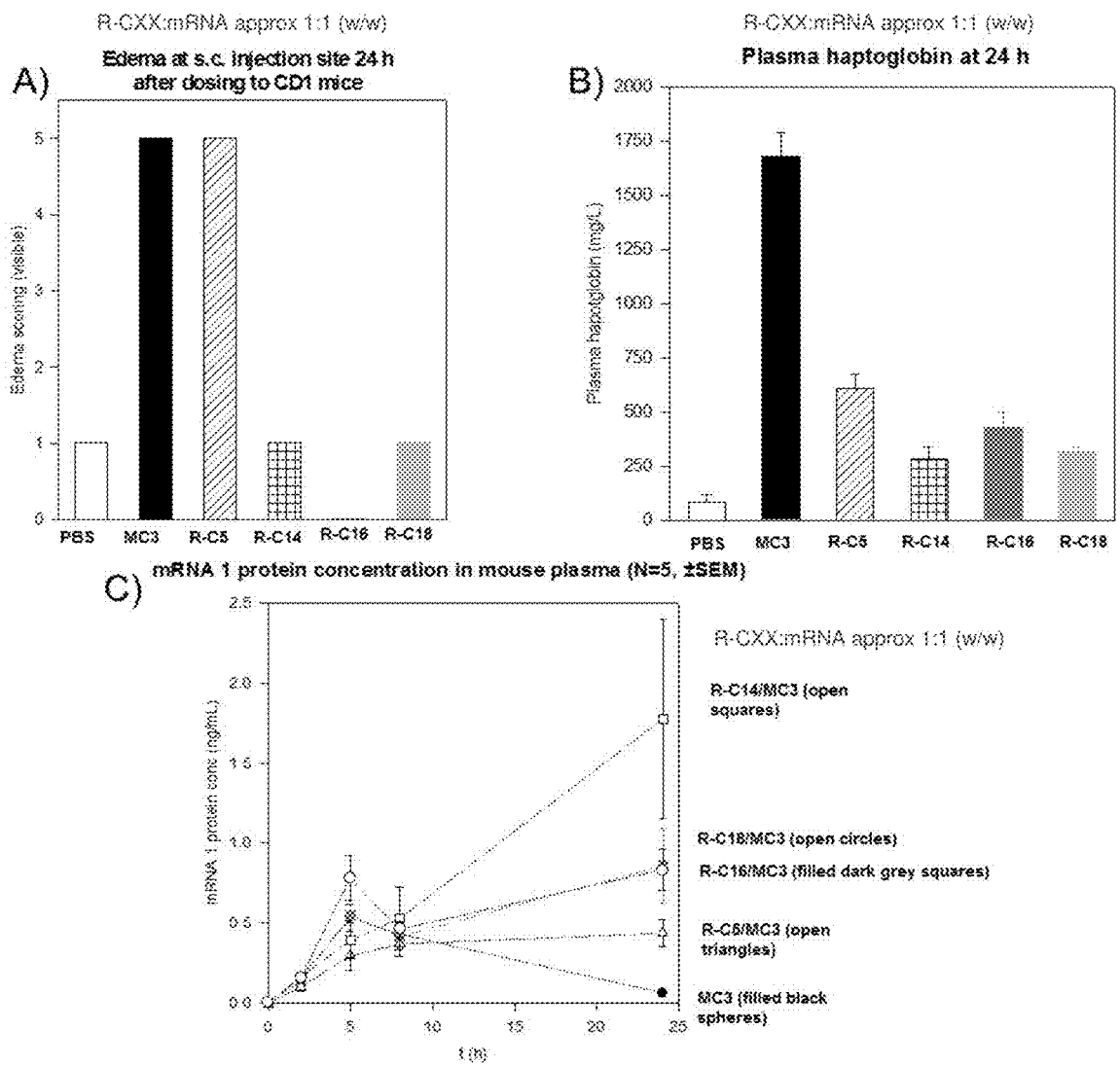
FIGS. 6A-C

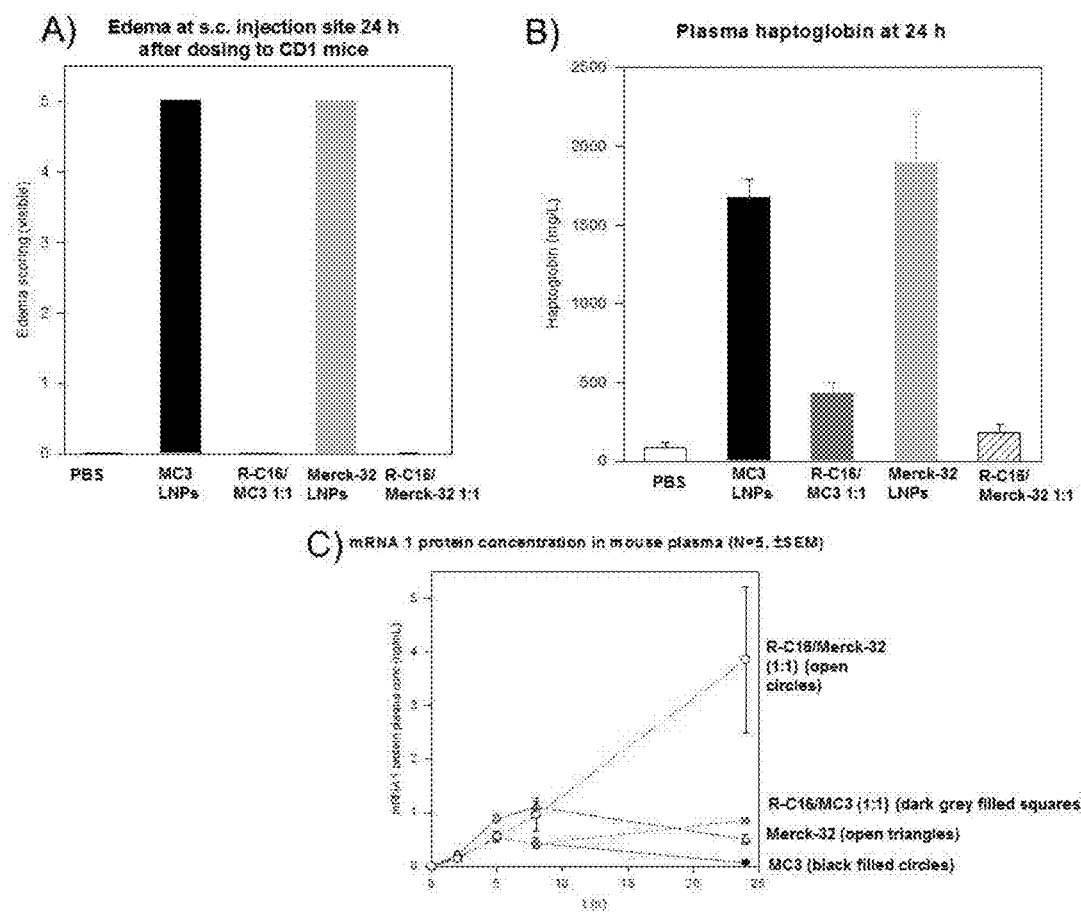
FIGS. 7A-C

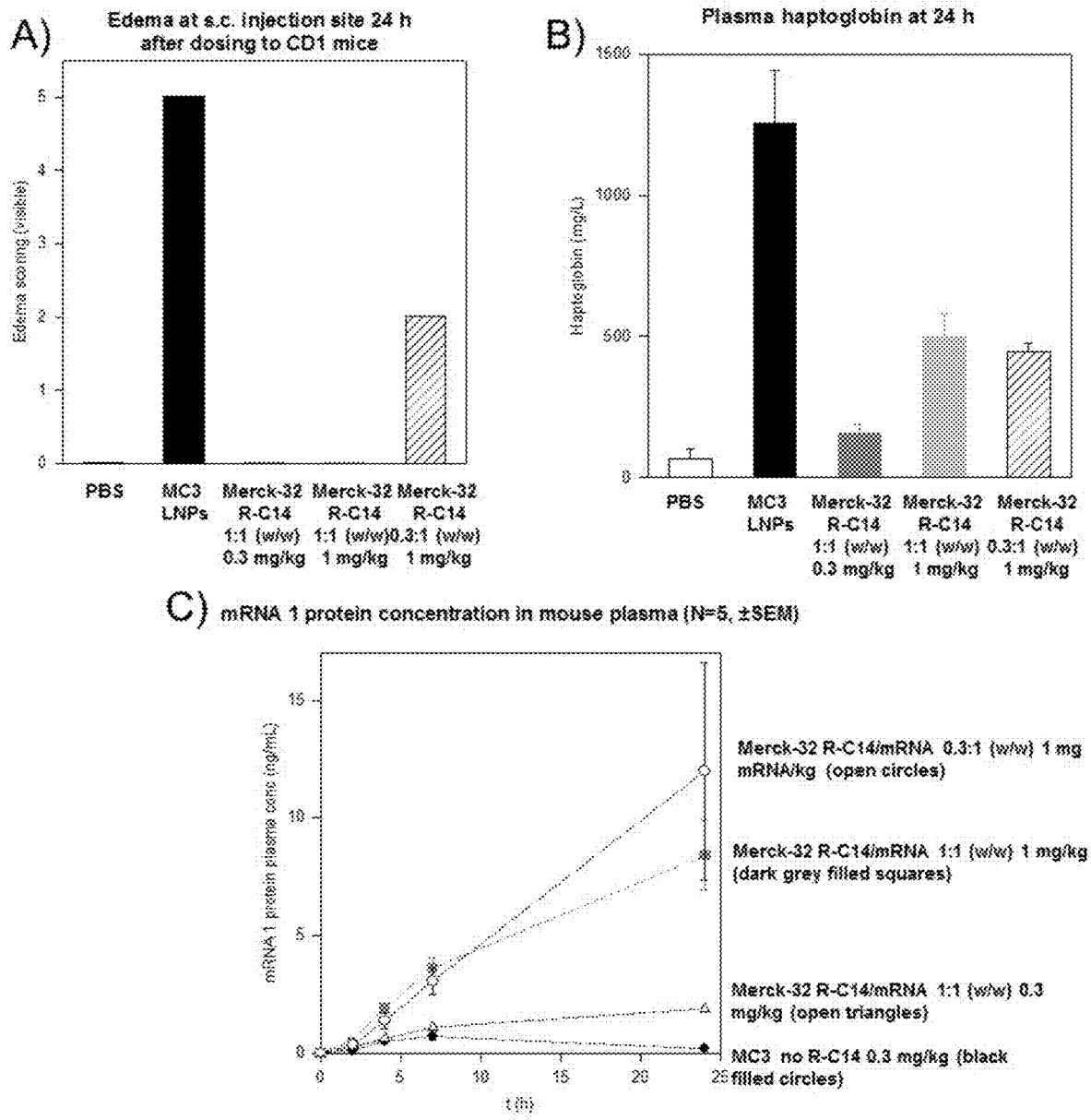
FIGS. 8A-C

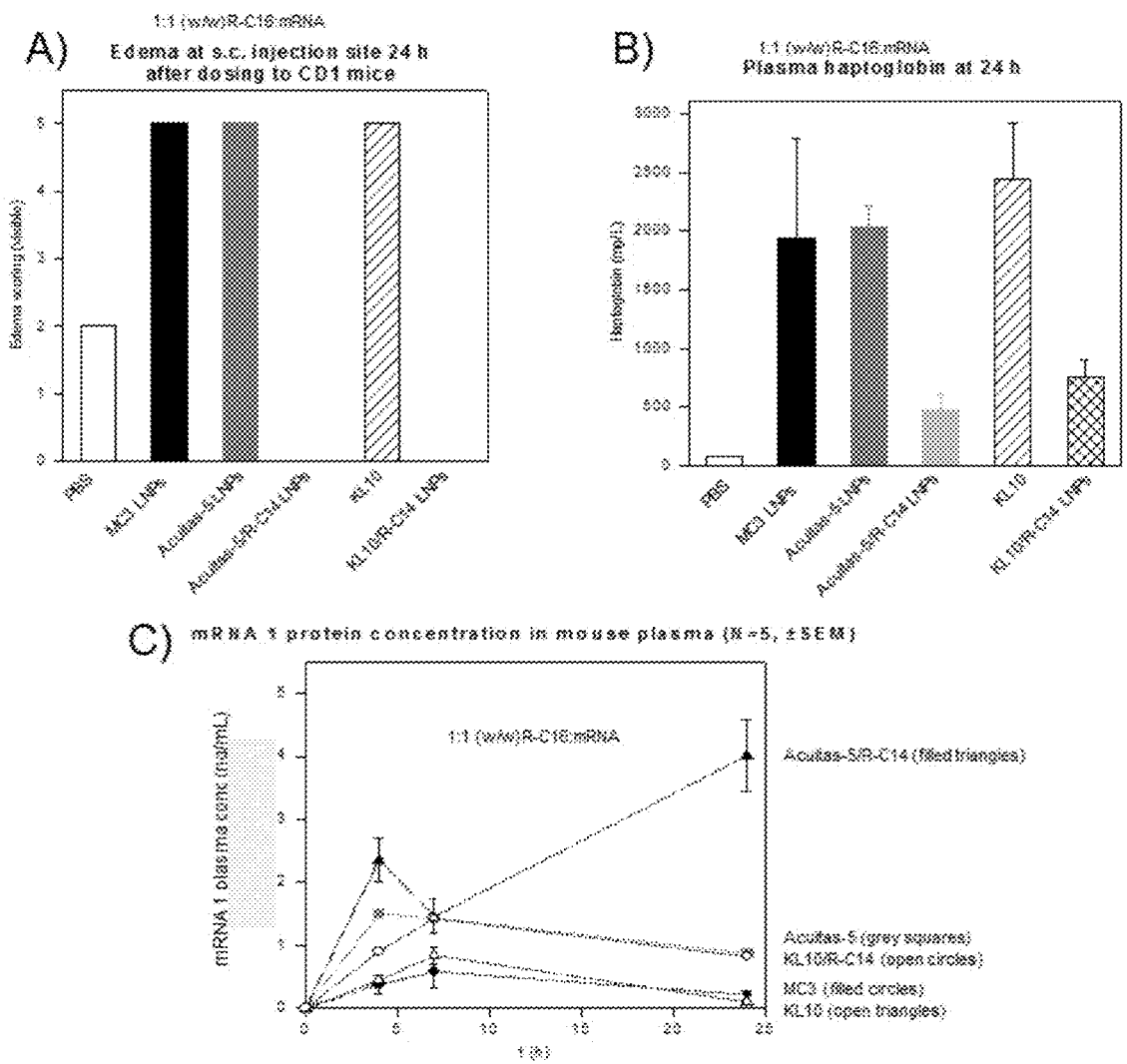
FIGS. 9A-C

LIPID NANOPARTICLES COMPRISING LIPOPHILIC ANTI-INFLAMMATORY AGENTS AND METHODS OF USE THEREOF

This application claims benefit under 35 U.S.C. § 119(e) of the following U.S. Provisional Application No. 62/333,574, filed May 9, 2016; U.S. Provisional Application No.: 62/359,429, filed Jul. 7, 2016; and US Provisional Application No.: 62/449,623, filed Jan. 24, 2017. Each of the above listed applications is incorporated by reference herein in its entirety for all purposes.

BACKGROUND

Safe and effective delivery of pharmaceutical active ingredients to target tissues and cells is of utmost importance in designing drug carriers. Known drug carriers, such as liposomes and lipid nanoparticles (LNPs), facilitate targeted, site-specific delivery of drugs to targeted tissues and cells, thus enhancing their bioavailability. However, a primary obstacle in developing such carriers is the immunogenic response associated with key components of these formulations.

Liposome carriers suitable for polynucleotide delivery often includes cationic lipid components enabling the delivery across the cellular membrane into the cytoplasm of the target cells. Such cationic liposomes are known to activate the immune system, which has been utilized in vaccines (Peer, D., Advanced Drug Delivery Reviews 64:1738-1748 (2012)). In contrast, LNPs are designed to have a zero net charge at physiological pH 7.4, thus reducing, although not completely eliminating the immune response associated with particles being positively charged. While liposomes may aid delivery of drugs to target tissues and cell, they also activate the immune system leading to an acute hypersensitivity reaction, which increases the risk of anaphylactic shock. (Kumar, V. et al., *Molecular Therapy-Nucleic Acids*, 3(e210): 1-7 (2014); Abrams, M T et al., *Molecular Therapy*, 18(1): 171-180 (2010)).

Despite efforts to minimize the immunogenic response associated with liposomes and LNPs such as adding a polyethylene glycol shield to LNPs to avoid recognition by the mononuclear phagocyte system and employing modified siRNA to minimize immunostimulation, they still elicit an immune response, thus limiting their effectiveness as therapeutic alternatives. (Kumar, V. et al., 2014, supra). Co-administration of an anti-inflammatory drug prior to liposome or LNP administration has also been investigated with limited results. (Tao, W. et al., *Molecular Therapy*, 19(3): 567-575 (2011); Abrams et al. (2010) supra). Pre-treatment with dexamethasone one hour prior to administration of LNP201, a liposome construct, partially inhibited inflammatory mRNAs, but did not eliminate the inflammatory effect. (Abrams et al. (2010) supra). Similar results were found in rats pre-treated with various anti-inflammatory drugs prior to LNP05-SSB siRNA or LNP05-Apo5 siRNA. (Tao, W. et al. (2011) supra).

The immunostimulatory effect of LNPs continues to block their use for safe and effective delivery of pharmaceutical drugs. Consequently, there exists a need to develop effective LNP delivery systems with an increased therapeutic window that do not trigger an inflammatory response.

SUMMARY

This specification discloses, in part, anti-inflammatory lipid nanoparticles comprising at least one lipophilic anti-inflammatory agent. In one embodiment, disclosed are anti-inflammatory lipid nanoparticles comprising a lipid phase and at least one lipophilic anti-inflammatory agent. In another embodiment, disclosed are anti-inflammatory lipid nanoparticles further comprising at least one nucleic acid segment.

In another embodiment, disclosed are pharmaceutical compositions comprising a plurality of anti-inflammatory lipid nanoparticles comprising a lipid phase, at least one lipophilic anti-inflammatory agent and a pharmaceutically acceptable carrier, diluent or excipient. In another embodiment, disclosed are pharmaceutical compositions comprising a plurality of anti-inflammatory lipid nanoparticles comprising a lipid phase, at least one lipophilic anti-inflammatory agent, and at least one nucleic acid segment, and a pharmaceutically acceptable carrier, diluent or excipient.

Also disclosed are methods for administering a pharmaceutical composition comprising a plurality of anti-inflammatory lipid nanoparticles to a subject in need thereof.

In another embodiment, disclosed is a method of delivering at least one nucleic acid segment to a target cell comprising contacting the cell with a pharmaceutical composition comprising a plurality of anti-inflammatory lipid nanoparticles and a therapeutically effective amount of at least one nucleic acid segment.

In another embodiment, disclosed is a method of delivering at least one nucleic acid segment to a subject in need thereof comprising administering to the subject a pharmaceutical composition comprising a plurality of anti-inflammatory lipid nanoparticles and a therapeutically effective amount of at least one nucleic acid segment.

Also disclosed is a method of treating a subject suffering from a disease or disorder comprising administering to the subject a pharmaceutical composition comprising a plurality of anti-inflammatory lipid nanoparticles and a therapeutically effective amount of at least one nucleic acid segment.

In another embodiment, disclosed are methods of inhibiting the immune response associated with non-anti-inflammatory LNP administration comprising administering to a subject a pharmaceutical composition comprising a plurality of anti-inflammatory lipid nanoparticles disclosed herein. The methods of inhibiting the immune response includes inhibiting the expression or activity of at least one biomarker or symptom of an immune response, for instance: (a) inhibiting the expression or activity of pro-inflammatory markers; (b) reducing inflammation (e.g., edema); and (c) reducing production of plasma haptoglobin associated with inflammation or an immune response.

In yet another embodiment, disclosed are methods for modulating protein or peptide expression in target cells of a subject in need thereof comprising administering an effective amount of a pharmaceutical composition comprising a plurality of anti-inflammatory lipid nanoparticles disclosed herein and a therapeutically effective amount of at least one nucleic acid segment In another embodiment, processes are disclosed for the preparation of the anti-inflammatory lipid nanoparticles. In one embodiment, disclosed is a process for the preparation of anti-inflammatory lipid nanoparticles comprising:
A) providing at least one aqueous solution optionally comprising at least one nucleic acid segment;
B) providing at least one organic solution comprising at least one lipophilic anti-inflammatory agent;

C) mixing the at least one aqueous solution with the at least one organic solution to produce a lipid nanoparticle solution containing a plurality of lipid nanoparticles.

DETAILED DESCRIPTION

BRIEF DESCRIPTION OF THE FIGURES

FIG. 1B illustrates the chemical structures of rofleponide and representative rofleponide prodrugs together with calculated octanol-water log (partition coefficient) using ACD Chemsketch 2014

FIGS. 2A-D illustrate (A): edema scoring at 24 hours post administration; (B): plasma haptoglobin concentration at 24 hours post administration; (C): plasma cytokine/chemokine concentrations at 8 and 24 hours post administration; and (D) mRNA 1 protein concentrations vs time after subcutaneous administration of PBS (phosphate buffer, pH 7.4), DLin-MC3-DMA based LNPs without and with rofleponide palmitate (R-C16).

FIGS. 3A-C illustrate (A): edema scoring at 24 hours post administration; (B): plasma haptoglobin concentration at 24 hours post administration; (C): mRNA1 protein concentrations vs time after subcutaneous administration of PBS (phosphate buffer, pH 7.4), DLin-MC3-DMA based LNPs without and with rofleponide palmitate (R-C16)/mRNA 1:1 w/w, 1:10 w/w, and 1:30 w/w.

FIGS. 4A-C illustrate (A): edema scoring at 24, 48 and 72 hours post administration; (B): plasma haptoglobin concentration vs. time; (C): mRNA 1 protein concentrations vs time after subcutaneous administration of LNPs containing rofleponide palmitate (R-C16) or rofleponide.

FIGS. 6A-C illustrate (A): edema scoring; (B): plasma haptoglobin concentration at 24 hours after administration; (C): mRNA 1 protein concentrations vs time after subcutaneous administration of LNPs containing rofleponide pro-drugs with different fatty acid chain lengths: rofleponide valerate (C5), rofleponide myristate (C14), rofleponide palmitate (C16), and rofleponide stearate (C18).

FIGS. 7A-C illustrate (A): edema scoring at 24 hours after administration; (B) plasma haptoglobin concentration at 24 hours after administration; (C) mRNA 1 protein concentrations vs time after subcutaneous administration of DLin-MC3-DMA and Merck-32 LNPs vs. DLin-MC3/rofleponide palmitate (R-C16), and Merck-32/rofleponide palmitate (R-C16)LNPs.

FIGS. 8A-C illustrate (A): edema scoring at 24 hours after administration comparing different dosages of mRNA 1; (B) plasma haptoglobin concentration at 24 hours after administration; (C) mRNA 1 protein concentrations vs time after subcutaneous administration of DLin-MC3-DMA and Merck-32 (with rofleponide myristate, R-C14) LNPs comparing different doses of mRNA 1.

FIGS. 9A-C illustrate (A): edema scoring at 24 hours after administration comparing different dosages of mRNA 1; (B) plasma haptoglobin concentration at 24 hours after administration; (C) mRNA 1 protein concentrations vs time after subcutaneous administration of DLin-MC3-DMA, KL10 (without/with R-C14) and Acuitas-5 (without/with R-C14) LNPs comparing different dosages of mRNA 1.

Anti-Inflammatory Lipid Nanoparticles

Figure 1A:
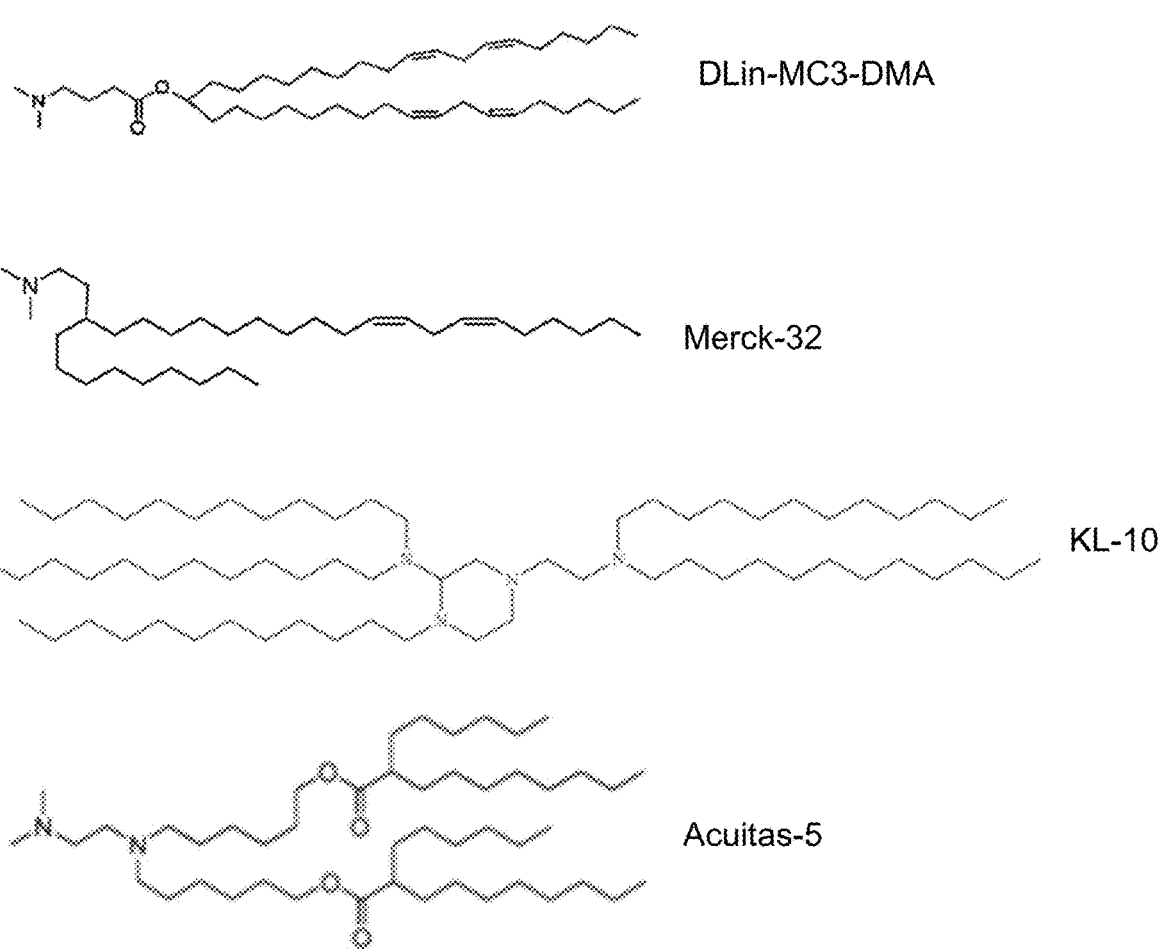
FIG. 1A illustrates the chemical structures of ionizable lipid components present in the anti-inflammatory lipid nanoparticles

According to the present disclosure, the anti-inflammatory lipid nanoparticles have an electron dense nanostructured core produced by microfluidic mixing of lipid-containing solutions in ethanol with aqueous solutions containing nucleic acid segment(s). It is to be understood that the anti-inflammatory lipid nanoparticles disclosed herein do not have continuous aqueous regions exceeding 50% by volume and thus, exclude conventional liposomes such as unilamellar vesicles and the like.

In one aspect, the anti-inflammatory lipid nanoparticles comprise a lipid phase and at least one lipophilic anti-inflammatory agent. The lipid nanoparticles may further comprise at least one nucleic acid segment.

One aspect of the present disclosure relates to anti-inflammatory lipid nanoparticles having an average particle size of about 200 nm in diameter or less, for example, less than or equal to about 100 nm, or, for instance, less than or equal to about 75 nm. In at least one embodiment of the present disclosure, the anti-inflammatory lipid nanoparticles have an average particle size ranging from about 50 nm to about 75 nm, for example, about 60 nm to about 65 nm, such as about 64 nm.

In certain embodiments, the anti-inflammatory lipid nanoparticles have an encapsulation efficiency (% EE) of nucleic acid segments of about 80% or higher, such as higher than about 90%, such as ranging from about 95%-100%, for example, about 99%. As used herein, the term "encapsulation efficiency" refers to the ratio of encapsulated nucleic acid segment in the anti-inflammatory lipid nanoparticles to total nucleic acid segment content in the pharmaceutical composition measured by lysis of the lipid nanoparticles using a detergent, e.g., Triton X-100. (See e.g., Leung et al. (2012) supra).

Lipid Phase

The lipid phase of the anti-inflammatory lipid nanoparticles disclosed herein may be constructed from any materials used in conventional nanoparticle technology, for example, ionizable lipids, neutral lipids, sterols, and polymer-conjugated lipids so long as the net charge of the nanoparticles is about zero.

Non-limiting examples of ionizable lipids include, for instance, lipids containing a positive charge at physiological pH, for example 1,2-dilinoleyloxy-3-dimethylaminopropane (DLin-DMA), dilinoleylmethyl-4-dimethylaminobutyrate (DLin-MC3-DMA, (see e.g., U.S. Pat. No. 8,158,601), 2-dilinoleyl-4-dimethylaminoethyl-[1,3]-dioxolane (DLin-KC2-DMA), Merck-32 (see e.g., WO 2012/018754), Acuitas-5 (see e.g., WO 2015/199952), KL-10 (see e.g., U.S. Patent Application Publication 2012/0295832), C12-200

(see e.g., Love, K T et al., *PNAS*, 107: 1864 (2009)), and the like. The ionizable lipids may be present in an amount ranging from about 5% to about 90%, such as from about 10% to about 80%, for instance from about 25% to about 75%, for example, from about 40% to about 60%, such as about 50%, molar percent, relative to the total lipid present in the anti-inflammatory lipid nanoparticles.

Neutral lipids have a zero net charge at physiological pH. Non-limiting examples of neutral lipids include those lipids that exist in an uncharged form or neutral zwitterionic form at physiological pH, such as distearoyl phosphatidylcholine (DSPC), dioleoyl phosphatidylethanolamine (DOPE), dipalmitoyl phosphatidylcholine (DPPC), dimyristoyl phosphatidylcholine (DMPC), and the like. The neutral lipids may be present in an amount ranging from about 1% to about 50%, such as from about 5% to about 20%, for example, 7.5% to about 12.5%, for instance, about 10%, molar percent, relative to the total lipid present in the anti-inflammatory lipid nanoparticles.

Non-limiting examples of sterols include cholesterol, and the like. The sterols may be present in an amount ranging from about 10% to about 90%, such as from about 20% to about 50%, for instance, from about 35%-45%, such as about 38.5%, molar percent, relative to the total lipid present in the anti-inflammatory lipid nanoparticles.

Polymer-conjugated lipids comprise a lipid portion and a polymer portion, such as pegylated lipids comprising both a lipid portion and a polyethylene glycol portion. Non-limiting examples include dimyristoyl phosphatidyl ethanolamine-poly(ethylene glycol) 2000 (DMPE-PEG2000), DPPE-PEG2000, DMG-PEG2000, DPG-PEG2000, PEG2000-c-DOMG, PEG2000-c-DOPG, and the like. The molecular weight of the poly(ethylene glycol) that may be used may range from about 500 and about 10; 000 Da, or from about 1,000 to about 5,000 Da.

The polymer-conjugated lipids may be present in an amount ranging from about 0% to about 20%, for example about 0.5% to about 5%, such as about 1% to about 2%, for instance, about 1.5%, molar percent, relative to the total lipid present in the anti-inflammatory lipid nanoparticles.

In at least one embodiment of the present disclosure, the anti-inflammatory lipid nanoparticles may be prepared by combining multiple lipid components. For example, the anti-inflammatory lipid nanoparticles may be prepared combining an ionizable lipid, a sterol, a neutral lipid, and a polymer-conjugated lipid at a molar ratio of $50:40-x_{PEG\ lipid}:10:X_{PEG\ lipid}$, with respect to the total lipids present. For example, the anti-inflammatory lipid nanoparticles may be prepared combining an ionizable lipid, a sterol, a neutral lipid, and a polymer-conjugated lipid at a molar ratio of 50:37:10:3 (mol/mol), or, for instance, a molar ratio of 50:38.5:10:1.5 (mol/mol), or, for example, 50:39.5:10:0.5 (mol/mol), or 50:39.75:10:0.25 (mol/mol).

In another embodiment, a lipid nanoparticle may be prepared using an ionizable lipid (such as DLin-DMA, DLin-KC2-DMA, DLin-MC3-DMA, Merck-32, KL10, or Acuitas-5), a sterol (such as cholesterol), a neutral lipid (such as DSPC), and a polymer conjugated lipid (such as DMPE-PEG2000) at a molar ratio of about 50:38.5:10:1.5 (mol/mol), with respect to the total lipids present. Yet another non-limiting example is an anti-inflammatory lipid nanoparticle comprising an ionizable lipid (such as DLin-DMA, DLin-KC2-DMA, DLin-MC3-DMA, Merck-32, KL10, or Acuitas-5), a sterol (such as cholesterol), a neutral lipid (such as DSPC), and a polymer conjugated lipid (such as DMPE-PEG2000) at a molar ratio of about 47.7:36.8:12.5:3 (mol/mol), with respect to the total lipids present.

Another non-limiting example is an anti-inflammatory lipid nanoparticle comprising an ionizable lipid (such as DLin-DMA, DLin-KC2-DMA, DLin-MC3-DMA, Merck-32, KL10, or Acuitas-5), a sterol (such as cholesterol), a neutral lipid (such as DSPC), and a polymer conjugated lipid (such as DMPE-PEG2000) at a molar ratio of about 52.4:40.4:6.4:0.8 (mol/mol), with respect to the total lipids present. In another embodiment, a non-limiting example is an anti-inflammatory lipid nanoparticle comprising an ionizable lipid (such as DLin-DMA, DLin-KC2-DMA, DLin-MC3-DMA, Merck-32, KL10, or Acuitas-5), a sterol (such as cholesterol), a neutral lipid (such as DSPC), and a polymer conjugated lipid (such as DMPE-PEG2000) at a molar ratio of about 53.5:41.2:4.6:0.7 (mol/mol), with respect to the total lipids present. Another non-limiting example is an anti-inflammatory lipid nanoparticle comprising an ionizable lipid (such as C12-200), a sterol (such as cholesterol), a neutral lipid (such as DSPC), and a polymer conjugated lipid (such as DMPE-PEG2000) at a molar ratio of about 30:50:19:1 (mol/mol), with respect to the total lipids present.

The selection of ionizable lipids, neutral lipids, sterols, and/or polymer-conjugated lipids that comprise the anti-inflammatory lipid nanoparticles, as well as the relative molar ratio of such lipids to each other, may be determined by the characteristics of the selected lipid(s), the nature of the intended target cells, and the characteristics of the nucleic acid, such as, for example, mRNA, to be delivered. For instance, in certain embodiments, the molar percent of ionizable lipid in the anti-inflammatory lipid nanoparticle may be greater than about 10%, greater than about 20%, greater than about 30%, greater than about 40%, greater than about 50%, greater than about 60%, or greater than about 70%, relative to the total lipids present. The molar percent of neutral lipid in the anti-inflammatory lipid nanoparticle may be greater than about 5%, greater than about 10%, greater than about 20%, greater than about 30%, or greater than about 40%, relative to the total lipids present. The molar percent of sterol in the anti-inflammatory lipid nanoparticle may be greater than about 10%, greater than about 20%, greater than about 30%, or greater than about 40%, relative to the total lipids present. The molar percent of polymer-conjugated lipid in the anti-inflammatory lipid nanoparticle may be greater than about 0.25%, such as greater than about 1%, greater than about 1.5%, greater than about 2%, greater than about 5%, or greater than about 10%, relative to the total lipids present.

According to the present disclosure, the anti-inflammatory lipid nanoparticles may comprise each of the ionizable lipids, neutral lipids, sterols, and/or polymer-conjugated lipids in any useful orientation desired. For example, the core of the nanoparticle may comprise an ionizable lipid and a sterol and one or more layers comprising neutral lipids and/or polymer-conjugated lipids may subsequently surround the core. For instance, according to one embodiment, the core of the anti-inflammatory lipid nanoparticle may comprise a core comprising an ionizable lipid (e.g., DLin-MC3-DMA), and a sterol (e.g., cholesterol) in any particular ratio, surrounded by a neutral lipid monolayer (e.g., DSPC) of any particular thickness, further surrounded by an outer polymer-conjugated lipid monolayer of any particular thickness. In such examples, the lipophilic anti-inflammatory agent and nucleic acid segment may be incorporated into any one of the core or subsequent layers depending upon the nature of the intended target cells, and the characteristics of the nucleic acid, such as, for example, mRNA, to be delivered. The core and outer layers may further comprise other components typically incorporated into lipid nanoparticles known in the art.

In addition, the molar percent of ionizable lipids, neutral lipids, sterols, and/or polymer-conjugated lipids that comprise the anti-inflammatory lipid nanoparticles may be selected in order to provide a particular physical parameter of the overall lipid nanoparticle, such as the surface area of one or more of the lipids. For example, the molar percent of ionizable lipids, neutral lipids, sterols, and/or polymer-conjugated lipids that comprise the anti-inflammatory lipid nanoparticles may be selected to yield a surface area per neutral lipid, for example, DSPC. By way of non-limiting example, the molar percent of ionizable lipids, neutral lipids, sterols, and/or polymer-conjugated lipids may be determined to yield a surface area per DSPC of about 1.0 nm$^2$ to about 2.0 nm$^2$, for example about 1.2 nm$^2$.

Lipophilic Anti-Inflammatory Agent

According to the present disclosure, the anti-inflammatory lipid nanoparticles further comprise a therapeutically effective amount of at least one lipophilic anti-inflammatory agent.

The terms "inflammation" and "inflammatory" refer to a biologic response involving an upregulation of the immune system, which may include an increase in protein activity related to inflammation or an immune response (e.g., pro-inflammatory markers such as chemokines and cytokines, production of plasma haptoglobin) and symptoms of inflammation (e.g., pain, heat, redness and/or edema). In some embodiments, inflammation is acute. In some embodiments, inflammation is chronic.

The term "anti-inflammatory agent" includes agents that elicit a biological or medical response in a subject that reduce inflammation (either acute or chronic) or downregulate the immune response, for example, by reducing or inhibiting enzyme or protein activity related to inflammation or an immune response (e.g., inhibition of pro-inflammatory markers or reduction in the production of plasma haptoglobin); by ameliorating one or more symptoms of inflammation or an immune response (e.g., pain, redness, heat or edema); or by slowing or delaying of the inflammatory process or the immune response.

The term "lipophilic anti-inflammatory agent" refers to anti-inflammatory agents exhibiting a log P value of about 5.0 or greater. The term "log P" refers to the determination of the logarithmic base-10 function of the Partition Coefficient, P; wherein P is the relative ratio of the concentration of a compound in an organic phase relative to the concentration of the same compound in an aqueous phase. The lipophilic nature of anti-inflammatory agents may be achieved by converting hydrophilic moieties of an anti-inflammatory agent to lipophilic moieties, for example, by converting a carboxyl group, amino group, hydroxyl group, or other hydrophilic group to an alkyl and alkyl esters, acid esters, aryl and aryl esters, heteroaryl esters, amide groups, or other lipophilic group. The lipophilic anti-inflammatory agents herein exhibit a log P value of about 5 or above. Lipophilic anti-inflammatory agents may be synthesized to increase their log P value by modifying the anti-inflammatory agent to become more lipophilic, as described above. The anti-inflammatory agent may be prepared via known techniques such as esterification or alkylation of one or more of any hydrophilic groups present on the parent drug molecule. (See e.g., Waring, M J, *Expert Opin. Drug Discov.*, 5(3): 235-248 (2010).

The term "therapeutically effective amount" preceding the at least one lipophilic anti-inflammatory agent refers to the amount of anti-inflammatory agent that inhibits and/or ameliorates any or all of the biomarkers or symptoms of an inflammatory response associated with the administration of non-anti-inflammatory LNPs.

The term "non-anti-inflammatory LNPs" refers to lipid nanoparticles that do not comprise an anti-inflammatory agent.

Known anti-inflammatory agents include, without limitation, corticosteroids (e.g., rofleponide, budesonide, etc.), and cytokine inhibitors (e.g., JAK1, JAK2, JAK3, TRL1-9, NF-κb, IRAK-1, IRAK-2, IRAK-4, IRF-3, TBK-1, TRAF-3, p38, IKKε, etc.), and the like.

In at least one embodiment of the present disclosure, the lipophilic anti-inflammatory agent is a rofleponide prodrug. Examples of rofleponide prodrugs include, but are not limited to rofleponide valerate (C5), rofleponide caproate (C6), rofleponide caprylate (C8), rofleponide caprate (C10), rofleponide laurate (C12), rofleponide myristate (C14), rofleponide palmitate (C16), or rofleponide stearate (C18).

In another embodiment, the lipophilic anti-inflammatory agent is a budesonide prodrug. Non-limiting examples include budesonide myristate (C14), budesonide palmitate (C16), budesonide stearate (C18), budesonide oleate (C18:1), and budesonide linoleate (C18:2).

The lipophilic anti-inflammatory agents may be present in an amount ranging from about 0.001% to about 50%, by weight, relative to the total weight of the anti-inflammatory lipid nanoparticles. In some embodiments, the lipophilic anti-inflammatory agents may be present in an amount ranging from about 0.5% to about 20%, such as about 1% to about 10%, for instance, about 8%, by weight, relative to the total weight of the anti-inflammatory lipid nanoparticles.

Nucleic Acid Segment

According to the present disclosure, the anti-inflammatory lipid nanoparticles may further comprise a therapeutically effective amount of a nucleic acid segment, which may be associated on the surface of the anti-inflammatory lipid nanoparticles and/or encapsulated within the same anti-inflammatory lipid nanoparticles.

The term "nucleic acid segment" is understood to mean any one or more nucleic acid segments selected from antisense oligonucleotides, DNA, mRNAs, siRNAs, Cas9-guideRNA complex, or combinations thereof. The nucleic acid segments herein may be wildtype or modified. In at least one embodiment, the anti-inflammatory lipid nanoparticles may comprise a plurality of different nucleic acid segments. In yet another embodiment, at least one of the nucleic acid segments, wildtype or modified, encodes a polypeptide of interest.

The term "therapeutically effective amount" preceding the at least one nucleic acid segment refers to an amount of nucleic acid sufficient to modulate protein expression in a target tissue and/or cell type. In some embodiments, a therapeutically effective amount of the at least one nucleic acid segment is an amount sufficient to treat a disease or disorder associated with the protein expressed by the at least one nucleic acid segment.

In at least one embodiment, the weight ratio of total lipid phase to nucleic acid segment ranges from about 40:1 to about 1:1, such as about 10:1. This corresponds to an approximate molar ratio of ionizable lipid to nucleic acid monomer of about 3:1. In yet another example, the weight ratio of total lipid phase to nucleic acid segment ranges from about 30:1 to about 1:1, such as about 17:1, which corresponds to an approximate molar ratio of ionizable lipid to nucleic acid monomer of about 6:1. However, the relative molar ratio of lipid phase and/or lipid phase components to the nucleic acid monomer may be determined by the nature of the intended target cells and characteristics of nucleic acid segment and thus, are not limited in scope to the above-identified embodiments.

In another embodiment, the anti-inflammatory lipid nanoparticles comprise lipophilic anti-inflammatory agents and nucleic acid segment in a weight ratio range of about 10:1 (lipophilic anti-inflammatory agents to nucleic acid segment) to about 1:100. In yet another embodiment, the weight ratio of nucleic acid segment to total lipids present in the lipid nanoparticles ranges from about 2:1 to about 1:50, such as about 1:1 to about 1:10.

Compositions

Pharmaceutical compositions of the present disclosure comprise the anti-inflammatory lipid nanoparticles disclosed herein, a therapeutically effective amount of at least one anti-inflammatory agent and a therapeutically effective amount of at least one nucleic acid segment, and/or one or more pharmaceutically acceptable excipient, carrier or diluent. As used herein, the term "pharmaceutically acceptable excipient, carrier or diluent" includes compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In certain embodiments, the pharmaceutical compositions may further comprise at least one tissue-targeting agent, for example, peptide conjugates such as DSPE-PEG3400-CRPPR or DSPE-CRPPR, and the like.

The pharmaceutical compositions may be in a form suitable for parenteral administration. Depending upon the therapeutic application, for in vivo administration, the compositions comprising anti-inflammatory lipid nanoparticles disclosed herein may be administered to a subject in need thereof intravenously, intradermally, intramuscularly, subcutaneously, sublingual, intratumorally, intracardiac, by intratracheal instillation, bronchial instillation, and/or inhalation.

The pharmaceutical compositions may be in the form of a sterile injectable aqueous or suspension, which may be formulated according to known procedures. A sterile injectable preparation may also be a sterile injectable suspension in a non-toxic parenterally-acceptable buffer. In other embodiments, the pharmaceutical composition may be lyophilized resulting in the form of a dry powder, wherein the dry powder can be later reconstituted for administration as needed. Dry powder compositions may further comprise bulking agents, for example, sucrose or trehalose.

Pharmaceutical liquid compositions can be nebulized by use of inert gases. Nebulized suspensions may be breathed directly from the nebulizing device or the nebulizing device can be attached to face masks tent, or intermittent positive pressure breathing machine. Furthermore, solid dosage forms may also be administered via inhalation using dry-powder inhalers. Suspension or dry powder pharmaceutical compositions can be administered orally or nasally from devices which deliver the pharmaceutical composition in an appropriate manner.

The amount of nucleic acid segment that is combined with one or more excipients to produce a single dosage form will necessarily vary depending upon the subject treated and the particular route of administration. For further information on routes of administration and dosage regimes the reader is referred to Chapter 25.3 in Volume 5 of Comprehensive Medicinal Chemistry (Corwin Hansch; Chairman of Editorial Board), Pergamon Press 1990.

Further provided herein is a pharmaceutical kit comprising a pharmaceutical composition comprising a therapeutically effective amount of at least one anti-inflammatory agent and a therapeutically effective amount of at least one nucleic acid segment, as herein disclosed. Such kits may further comprise various conventional pharmaceutical kit components such as containers comprising pharmaceutically-acceptable adjuvants, diluents or carriers, and additional containers readily apparent to those skilled in the art. Instructions, either as inserts or as labels, indicating quantities of the components to be administered, guidelines for administration, and/or guidelines for mixing the components, can also be included in the kit.

Methods

In one embodiment, the present disclosure provides a method for administering pharmaceutical compositions comprising a plurality of anti-inflammatory lipid nanoparticles to a subject in need thereof.

The term "subject" includes warm-blooded mammals, for example, primates, cows, pigs, sheep, dogs, cats, rabbits, rats, and mice. In some embodiments, the subject is a primate, for example, a human. In some embodiments, the subject is in need of treatment (e.g., the subject would benefit biologically or medically from treatment).

The anti-inflammatory lipid nanoparticles disclosed herein may further serve as platforms for selective delivery of, for example, nucleic acid segments to target cells and tissues, such as antisense oligonucleotides, DNA, mRNAs, siRNAs, Cas9-guideRNA complex. Thus, in one embodiment, is a method of delivering at least one nucleic acid segment to a cell comprising contacting the cell, in vitro or in vivo, with a pharmaceutical composition comprising a plurality of anti-inflammatory lipid nanoparticles and a therapeutically effective amount of at least one nucleic acid segment. In some embodiments, the nucleic acid segment modulates expression, for example, by increasing or decreasing expression, or by upregulating or downregulating expression of the polypeptide.

Another embodiment provides a method for delivering a therapeutically effective amount of at least one nucleic acid segment to a subject in need thereof, comprising administering to the subject a pharmaceutical composition comprising a plurality of anti-inflammatory lipid nanoparticles and a therapeutically effective amount of at least one nucleic acid segment.

The pharmaceutical compositions comprising a plurality of anti-inflammatory lipid nanoparticles and at least one nucleic acid segment disclosed herein may be used to treat a wide variety of disorders and diseases characterized by underexpression of a polypeptide in a subject, overexpression of a polypeptide in a subject, and/or absence/presence of a polypeptide in a subject. Accordingly, disclosed are methods of treating a subject suffering from a disease or disorder comprising administering to the subject a pharmaceutical composition comprising a plurality of anti-inflammatory lipid nanoparticles and a therapeutically effective amount of at least one nucleic acid segment.

Disclosed further are methods of inhibiting the immune response associated with non-anti-inflammatory LNP administration comprising administering a pharmaceutical composition comprising a plurality of anti-inflammatory lipid nanoparticles comprising a therapeutically effective amount of at least one lipophilic anti-inflammatory agent to a subject in need thereof. For example, the anti-inflammatory lipid nanoparticles according to the present disclosure may inhibit and/or ameliorate the expression or activity of at least one biomarker or symptom of an immune response. In at least one embodiment, the methods disclosed herein reduce and/or inhibit inflammation at the injection site (as determined by edema scoring), reduce and/or inhibit production of plasma haptoglobin, and reduce and/or inhibit the amount of pro-inflammatory markers (e.g., cytokines, chemokines). Thus, the present disclosure includes methods for inhibiting the expression or activity of pro-inflammatory markers, reducing inflammation (e.g., edema), and for reducing production of plasma haptoglobin, comprising administering a pharmaceutical composition comprising a plurality of anti-inflammatory lipid nanoparticles comprising a therapeutically effective amount of at least one lipophilic anti-inflammatory agent and a therapeutically effective amount of at least one nucleic acid segment.

In at least one embodiment, a reduction or inhibition of edema is observed. In another embodiment, a reduction or inhibition in plasma haptoglobin levels is observed. In yet another embodiment, a reduction or inhibition of plasma inflammatory markers in observed. In any one of the disclosed methods, the target activity of the encapsulated nucleic acid segment is not inhibited. For instance, methods are disclosed for increasing protein expression in cells, comprising administering a pharmaceutical composition comprising a plurality of anti-inflammatory lipid nanoparticles disclosed herein comprising a therapeutically effective amount of at least one anti-inflammatory agent and a therapeutically effective amount of at least one nucleic acid segment.

Non-limiting examples of pro-inflammatory markers include cytokines and chemokines, for instance, IL-1, IL-2, IL-3, IL-4, IL-5, IL-6, IL-8, IL-9, IP-10, IL-12 (p40), IL-12 (p70), IL-13, IL-15, IL-16, IL-17, Exotaxin, FGF-basic, G-CSF, GM-CSF, LIF, MIG, MIP-1, MIP-2, MCP-1, INF-γ, INFα2, RANTES, TNFα, and IL-1β. For example, the methods disclosed herein reduce and/or inhibit edema, and reduce and/or inhibit the production of plasma haptoglobin and/or reduce and/or inhibit the production of pro-inflammatory markers associated with non-anti-inflammatory LNP administration by a percentage greater than the control levels.

As used herein, the term "reduce and/or inhibits" refers to a change (positive or negative) of about 10, 20, 30, 40, 50, 60, 70, 80, 90 percent or greater as compared to a control level. As used herein, the term "control level" indicates an untreated sample or subject, or a sample or subject treated with lipid nanoparticles without the disclosed lipophilic anti-inflammatory agent. By way of example, a control level is the level of expression or activity in a control sample in the absence of a lipophilic anti-inflammatory agent.

For example, the methods disclosed herein reduce and/or inhibit the production of IL-6, IL-8, KC, IP-10, and MCP-1 by a percentage of about 80% or greater, comprising administering a pharmaceutical composition comprising a plurality of anti-inflammatory lipid nanoparticles to a subject in need thereof, for instance about 85% or greater.

Also disclosed herein are methods for inhibiting edema at the injection site associated with non-anti-inflammatory LNP administration, wherein the method comprises administering a pharmaceutical composition comprising a plurality of anti-inflammatory lipid nanoparticles to a subject in need thereof. For example, the methods disclosed herein produce substantially no edema at the injection site. As used herein, the term "substantially no edema" is understood to mean no visible swelling and/or redness apparent to the naked eye.

Also disclosed are methods for inhibiting production of plasma haptoglobin associated with non-anti-inflammatory LNP administration, comprising administering a pharmaceutical composition comprising a plurality of anti-inflammatory lipid nanoparticles to a subject in need thereof. According to at least one embodiment, the methods herein inhibit the production of plasma haptoglobin by a percentage of about 60% or greater comprising administering a pharmaceutical composition comprising a plurality of anti-inflammatory lipid nanoparticles to a subject in need thereof, for instance about 80% or greater. In another embodiment, the methods herein comprise administering a pharmaceutical composition comprising a plurality of anti-inflammatory lipid nanoparticles to a subject in need thereof while maintaining normal plasma haptoglobin levels. As used herein, the term "normal plasma haptoglobin levels" includes plasma haptoglobin levels in the range of 3200 ng/mL-65000 ng/m L.

Further disclosed are methods for increasing protein expression in cells, comprising administering a pharmaceutical composition comprising a plurality of anti-inflammatory lipid nanoparticles disclosed herein, to a subject in need thereof. In at least one embodiment, protein expression may be increased by a factor of about 2 up to 24 hours. In another embodiment, protein expression may be increased by a factor of about 3 up to 72 hours.

EXAMPLES

Aspects of the present disclosure can be further defined by reference to the following non-limiting examples, which describe in detail preparation of lipid nanoparticles and compositions of the present disclosure and methods for using lipid nanoparticles of the present disclosure. It will be apparent to those skilled in the art that many modifications, both to materials and methods, can be practiced without departing from the scope of the present disclosure.

Preparation of LNPs Containing mRNA

Figure 1C:
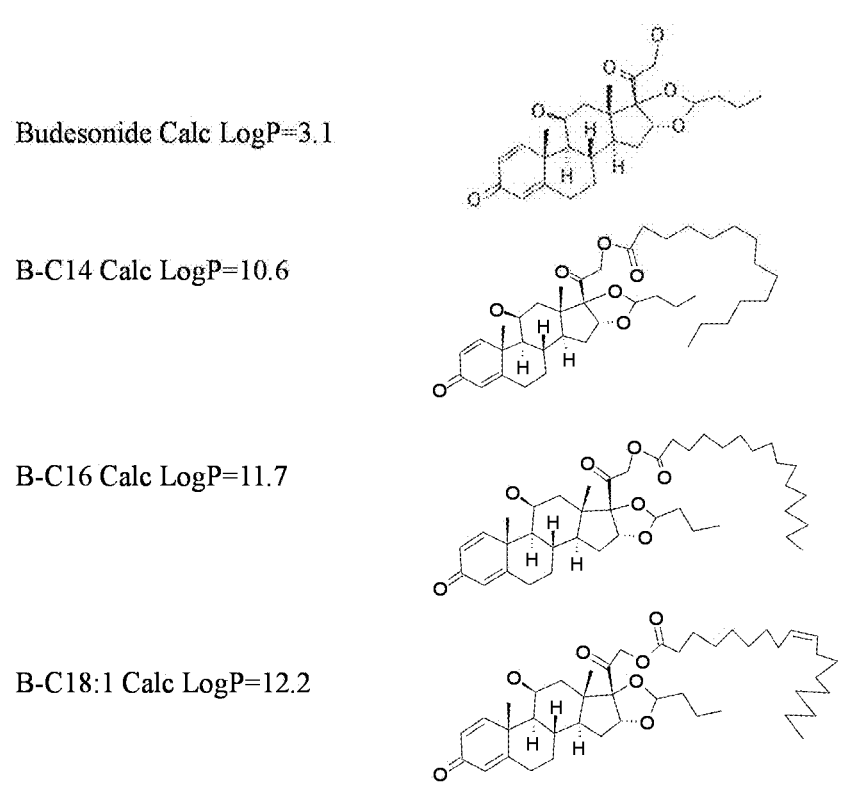
FIG. 1C illustrates the chemical structures of budesonide, and representative budesonide prodrugs together with calculated octanol-water log (partition coefficient) using ACD Chemsketch 2014.

A solution of mRNA 1 in citrate buffer was prepared by mixing mRNA 1 dissolved in MilliQ-water, 100 mM citrate buffer (pH 3) and MilliQ-water to give a solution of 50 mM citrate. A lipid solution in ethanol (99.5%) was prepared with four different lipid components: ionizable lipid (DLin-MC3-DMA, Merck-32, KL10 or Acuitas-5); cholesterol (Sigma-Aldrich); DSPC (distearoyl phosphatidyl choline, Avanti Polar Lipids Inc); and DMPE-PEG2000 (dimyristoyl phosphatidyl ethanolamine-poly(ethylene glycol) 2000, NOF Corporation). The chemical structures of the ionizable lipids are shown in FIG. 1A. The total concentration of lipids in all experiments was 12.5 mM. Lipid nanoparticles containing lipophilic anti-inflammatory agent pro-drugs were prepared by adding pro-drug to the lipidic ethanol solution. The chemical structures of rofleponide, and the different pro-drugs abbreviated as R-C5, R-C14. R-C16 and R-C18 based on the lengths of the fatty acid chains, are shown in FIG. 1B. The chemical structures of budesonide, and the different pro-drugs abbreviated as B-C14, B-C16 and B-C18:1 based on the lengths of the fatty acid chains, are shown in FIG. 1C.

The mRNA and lipid solutions were mixed in a NanoAssemblr (Precision Nanosystems, Vancouver, BC, Canada) microfluidic mixing system at a mixing ratio of Aq:EtOH=3:1 and a constant flow rate of 12 mL/min. At the time of mixing the ratio between the nitrogen atoms on the ionizable lipid and phosphorus atoms on the mRNA chain was equal to 3.1.

The first 0.2-0.35 mL and the last 0.05-0.1 mL of the LNP suspension prepared were discarded while the rest of the volume was collected as the sample fraction. From the sample fraction 25 µL of sample was injected into 975 µL 10 mM phosphate buffer pH 7.4 and used to measure the intensity averaged particle size on a Malvern ZetaSizer (ZetaSizer Nano ZS, Malvern Instruments Inc., Westborough, Mass., USA) ("pre-dialysis particle size") and polydispersity index (PDI). The remaining sample volume was transferred immediately to a Slide-a-lyzer G2 dialysis cassette (10000 MWCO, ThermoFischer Scientific Inc.) and dialyzed over night at 4° C. against PBS (pH7.4). The volume of the PBS buffer was 500-1000x the sample fraction volume. The sample fraction was then collected and from this volume 25 µL was injected into 975 µL 10 mM phosphate buffer, pH 7.4, and the particle size was measured once again (post dialysis particle size) as well as PDI.

The final mRNA concentration and encapsulation efficiency percentage (% EE) was measured by Quant-it Ribogreen Assay Kit (ThermoFischer Scientific Inc.) using Triton-X100 to disrupt the LNPs.

In Vivo Mouse Experiments

Different groups of 5 mice (female, age~12 weeks, Crl: Cd1(ICR), Charles River) were administered with PBS (negative control) or mRNA 1 formulated in lipid nanoparticles. Prior to administration, the mice were lightly anaesthetized with Isoflurane 5% and the injection area was shaved. The formulations were then injected subcutaneously (5 ml/kg or 0.3 mg mRNA/kg) in the intrascapular region to different groups of mice. Post-dose blood samples were collected and plasma was prepared by centrifugation. Aliquots of plasma were transferred into cryo tubes (0.5 ml U-shaped polypropylene cryotubes (Sarstedt Microtube with cap Ref #72.730) and stored frozen until quantification of haptoglobin, cytokines/chemokines and mRNA 1 protein concentrations. In some studies, quantification was also carried out of lipophilic anti-inflammatory agent in plasma samples. At 24 hours after administration, clinical signs of inflammatory response was evaluated by gently pressing the finger over the injection area to determine edema and judged by visual inspection as edema or no edema in the different mice. The number of mice displaying visible signs of edema per group (each group having 5 mice) was summed to give an edema score of 0-5.

Quantification of Haptoglobin in Plasma

Plasma concentrations of haptoglobin were measured by EMD Millipore's MILLIPLEX® MAP Mouse Acute Phase panel 2 kit (Merck KGaA, Darmstadt, Germany). The sample was first diluted 1:20 000 with Assay buffer then, together with standard's and QC's placed in a 96 well plate. A solution containing beads were then added. The beads were magnetic microspheres each of which was coated with a specific antibody. The mixture was incubated over night at 4° C. and the reaction mixture was then incubated with Streptavidin-PE conjugate to complete the reaction on the surface of each microsphere. The plate was read on analyzer Luminex® 100. Each individual microsphere was identified and the result of its bioassay quantified based on fluorescent reporter signals. The concentration was measured using Median Fluorescent Intensity (MFI) data using a 5-parameter logistic curve-fitting method.

Quantification of Cytokines/Chemokines in Plasma

Plasma concentrations of murine cytokines/chemokines were measured by EMD Millipore's MILLIPLEX® MAP Mouse Cytokine magnetic bead kit (Merck KGaA, Darmstadt, Germany) for the simultaneous quantification of cytokines; IL-6, KC, MCP-1 and IP-10. The samples were first diluted 1:2 with Assay buffer then, together with standard's and QC's placed in a 96 well plate. A solution containing beads were added. The beads are magnetic microspheres each of which is coated with a specific antibody. The mixture was incubated over night at 4° C. and the reaction mixture was then incubated with Streptavidin-PE conjungate to complete the reaction on the surface of each microsphere. The plate was read on analyzer Luminex® 100. Each individual microsphere was identified and the result of its bioassay quantified based on fluorescent reporter signals. The concentration was measured using Median Fluorescent Intensity (MFI) data using a 5-parameter logistic curve-fitting method.

Quantification of mRNA 1 Protein in Plasma mRNA 1 protein was measured as a single analyte with the Milliplex Human Liver Protein Magnetic beads [Merck Millipore, Darmstadt, Germany]. The assay was performed using the Bioplex Multiplex Suspension Array System, Luminex 100TM] and Bioplex Manager 6.1 software curve fitting software [Bio-Rad Laboratories, Hercules, Calif.]. Briefly, the assay was performed according to a modified protocol based upon the manufacturers' instruction, with additional calibration points to extend the lower range of the standard curve. Sample data was back calculated from the standard curve (5PL curve fitting).

Quantification of Lipophilic Anti-Inflammatory Agent in Plasma

The concentration of lipophilic anti-inflammatory agent in plasma was determined by protein precipitation followed by liquid chromatography with mass spectrometric detection. An 50 μL plasma sample was precipitated with 180 μL 0.2% formic acid in acetonitrile containing 10 nmol/L of 5,5-Diethyl-1,3-Diphenyl-2-Iminobarbituric acid as volume marker. After vortex for 3 min and centrifugation (4000 rpm, 4° C., 20 min), the supernatant was taken and analyzed. Analysis of the supernatant was performed on a short reversed-phase HPLC column with rapid gradient elution and MS/MS detection using a triple quadrupole instrument with electrospray ionisation and Multiple Reaction Monitoring (MRM) acquisition.

Example 1: LNPs Containing Rofleponide Palmitate/mRNA (1:1 w/w)

The molar composition of the lipids used to prepare the lipid solution was DLin-MC3-DMA:DSPC:Cholesterol:DMPE-PEG2000=50:10:38.5:1.5 (mol/mol). In addition, the solution also contained rofleponide palmitate (R-C16) at an amount which resulted in a total concentration of R-C16=0.25 mM in the pre-dialysis LNP solution. The final molar composition of the four lipids and R-C16 in the LNPs are stated in Table 1 below.

An 1.05 mL aliquot of mRNA 1 solution and 0.35 mL of lipid and R-C16 solution were mixed according to the process described above. Furthermore, amorphous R-C16 nanoparticles containing only the R-C16 and DMPE-PEG2000 ("R-C16 control") were prepared under the same mixing conditions as described above. The particle size was measured immediately after preparation using the protocol described for the LNPs after which these particles were dialyzed as well. The measured pre- and post-dialysis particle sizes and the % EE are presented in Table 1a below.

TABLE 1a

Final molar compositions, measured particle sizes and % EE of samples S1 and S2

| Sample | Composition [mol %] | pre-dialysis | | post-dialysis | | |
|---|---|---|---|---|---|---|
| | | Size [nm] | PDI | Size [nm] | PDI | % EE |
| S1 | MC3:DSPC:Cholesterol:DMPE-PEG2000:R-C16 46.29:9.20:35.61:1.48:7.42 | 76 | 0.004 | 80 | 0.06 | 97 |
| S2 | R-C16 control | 193 | 0.26 | 47 | 0.26 | — |

To determine the amount of rofleponide palmitate (R-C16) incorporated in the LNPs, 900 μL of the samples was ultracentrifuged at 500000 g for 60 min and the bottom fraction of 300 μL and the original sample (not centrifuged) were analyzed for DLin-MC3-DMA and R-C16 content using a HPLC with signals detected using a PDA-CAD detector. The CAD signal was used for DLin-MC3-DMA and, for R-C16, the UV-absorbance maximum at 235 nm was used and the concentrations determined with an external standard curve. The analyzed ratio between the two components was compared with the ratio in the original sample. In addition, the concentration of R-C16 in the different fractions from the LNP samples was compared to the concentration of R-C16 in samples containing nanoparticles of only R-C16 and DMPE-PEG2000 ("R-C16 control"). Analysis of the "R-C16 control" sample showed that after ultracentrifugation the rofleponide palmitate was completely located in the bottom phase unlike the LNP sample containing R-C16. This indicates that rofleponide palmitate, which is completely insoluble in water, does not form separate drug particles in the mixture but rather is incorporated into the LNPs.

The HPLC results for the R-C16 LNPs are shown in Table 1b. The ratio between the DLin-MC3-DMA and the R-C16 is similar in all fractions and close to what is seen in the original sample indicating incorporation of rofleponide palmitate (R-C16) in the LNPs.

TABLE 1b

The analyzed weight ratio between Dlin-MC3-DMA and R-C16 in the original and ultracentrifuged bottom phase sample

| Sample | Fraction | Dlin-MC3-DMA:R-C16 ratio (w/w) |
|---|---|---|
| R-C16 1:1 | Original | 0.78 |
|  | Bottom | 0.77 |

Example 2: Non-Anti-Inflammatory LNPs Vs. Rofleponide Palmitate/mRNA (1:1 w/w) LNPs The molar composition of the lipids used to prepare the lipid solution was DLin-MC3-DMA:DSPC:Cholesterol:DMPE-PEG2000=50:10:38.5:1.5. In addition, for sample S4 the solution also contained rofleponide palmitate (R-C16) at an amount which resulted in a total concentration of R-C16=0.25 mM in the pre-dialysis LNP solution. The final molar composition of the four lipids and R-C16 in the LNPs are stated in Table 2 below. 1.05 mL of mRNA 1 solution and 0.35 mL of lipid and R-C16 solution was mixed according the general description. The measured pre- and post-dialysis particle sizes as well the % EE are presented in Table 2 below.

TABLE 2

Final molar compositions, measured particle sizes and % EE of samples S3 and S4.

| Sample | Composition [mol %] | Pre-dialysis Size [nm] | PDI | post-dialysis Size [nm] | PDI | % EE |
|---|---|---|---|---|---|---|
| S3 | MC3:DSPC:Cholesterol:DMPE-PEG2000 50:10:38.5.1.5 | 77 | 0.02 | 79 | 0.05 | 98 |
| S4 | MC3:DSPC:Cholesterol:DMPE-PEG2000:R-C16 46.29:9.20:35.61:1.48:7.42 | 87 | 0.02 | 83.1 | 0.04 | 98 |

Phosphate buffer (PBS) and samples S3 and S4 were administered subcutaneously to different groups of mice (N=5) at a dose of 0.3 mg mRNA/kg as described above. The results obtained for edema scoring, plasma haptoglobin, plasma cytokines/chemokines and plasma mRNA 1 protein concentrations are shown in FIGS. 2A-D. The data for cytokines/chemokines are shown at both 8 and 24 hours. The results show that by using LNPs according to the present disclosure, biomarkers or symptoms of an immune response such as inflammation (measured as edema scoring), haptoglobin and cytokines/chemokine in plasma, are significantly reduced. In addition, the LNPs according to the present disclosure give rise to an increased protein expression.

Example 3: Non-Anti-Inflammatory LNPs Vs. Rofleponide Palmitate/mRNA (1:1, 1:10 and 1:30 w/w) LNPs The molar composition of the lipids used to prepare the lipid solution was DLin-MC3-DMA:DSPC:Cholesterol:DMPE-PEG2000=50:10:38.5:1.5. In addition, for sample S5, S6 and S7, the solution also contained rofleponide palmitate (R-C16) at an amount which resulted in a total concentration of R-C16=0.25 mM (S5), 0.025 mM (S6) or 8.3 μM (S7) in the pre-dialysis LNP solution. The final molar composition of the four lipids and R-C16 in the LNPs are stated in Table 3 below. 1.29 mL of mRNA 1 solution and 0.43 mL of lipid and R-C16 solution was mixed according to the description above. The measured pre- and post-dialysis particle sizes as well the % EE are presented in Table 3 below.

TABLE 3

Final molar compositions, measured particle sizes and % EE of samples S5-S8

| Sample | Composition [mol %] | pre dialysis Size [nm] | PDI | post dialysis Size [nm] | PDI | % EE |
|---|---|---|---|---|---|---|
| S5 | MC3:DSPC:Cholesterol:DMPE-PEG2000 50:10:38.5:1.5 | 75 | 0.03 | 91 | 0.14 | 98 |
| S6 | MC3:DSPC:Cholesterol:DMPE-PEG2000:R-C16 46.29:9.20:35.61:1.48:7.42 | 101 | 0.17 | 84 | 0.07 | 97 |
| S7 | MC3:DSPC:Cholesterol:DMPE-PEG2000:R-C16 49.61:9.86:38.16:1.59:0.79 | 77 | 0.01 | 85 | 0.12 | 98 |
| S8 | MC3:DSPC:Cholesterol:DMPE-PEG2000:R-C16 49.87:9.91:38.36:1.60:0.26 | 81 | 0.01 | 89 | 0.16 | 98 |

Phosphate buffer (PBS) and samples S5-S8 were administered subcutaneously to different groups of mice (N=5) at a dose of 0.3 mg mRNA/kg as described above. The results obtained for edema scoring, plasma haptoglobin, and plasma protein concentrations are shown in FIGS. 3A-C. The results show that by using R-C16 LNPs (at all ratios), inflammation measured as edema scoring and haptoglobin is significantly reduced. In addition, the R-C16 LNPs (at all ratios) give rise to an increased protein expression vs. non-anti-inflammatory DLin-MC3-DMA LNPs.

Example 4: Rofleponide Palmitate Vs. Rofleponide LNPs

The molar composition of the lipids used to prepare the lipid solution was DLin-MC3-DMA:DSPC:Cholesterol:DMPE-PEG2000=50:10:38.5:1.5. In addition, for sample S9, the solution also contained rofleponide palmitate (R-C16) at an amount which resulted in a total concentration of R-C16=0.25 mM in the pre-dialysis LNP solution. For this sample, 1.05 mL of mRNA 1 solution and 0.35 mL of lipid and R-C16 solution was mixed according to the description above. Sample S10 was prepared by adding a 16 µL ethanol solution of 21 mM rofleponide to DLin-MC3-DMA:DSPC:Cholesterol:DMPE-PEG2000 LNPs, after the dialysis step, to give the desired composition and was thereafter equilibrated for 2 days. The final molar composition of the four lipids and R-C16 or rofleponide in the LNPs is stated in Table 4 below. The measured pre- and post-dialysis particle sizes as well the % EE are presented in Table 4 below (for the size measurement PBS, pH 7.4, was used).

Phosphate buffer (PBS) samples S9 and S10 were administered subcutaneously to two groups of mice (N=15) at a dose of 0.3 mg mRNA/kg as described above. The results obtained for edema scoring, plasma haptoglobin, and plasma protein concentrations are shown in FIGS. 4A-C. The results show that by using R-C16 LNPs according to the present disclosure, inflammation measured as edema scoring and haptoglobin is significantly reduced vs. the LNPs containing the rofleponide at the same molar dose. In addition, the R-C16 LNPs give rise to an increased and prolonged protein expression protein vs. LNPs containing the rofleponide.

Example 5: Conversion of Pro-Drug Rofleponide Palmitate to Rofleponide

Figure 5:
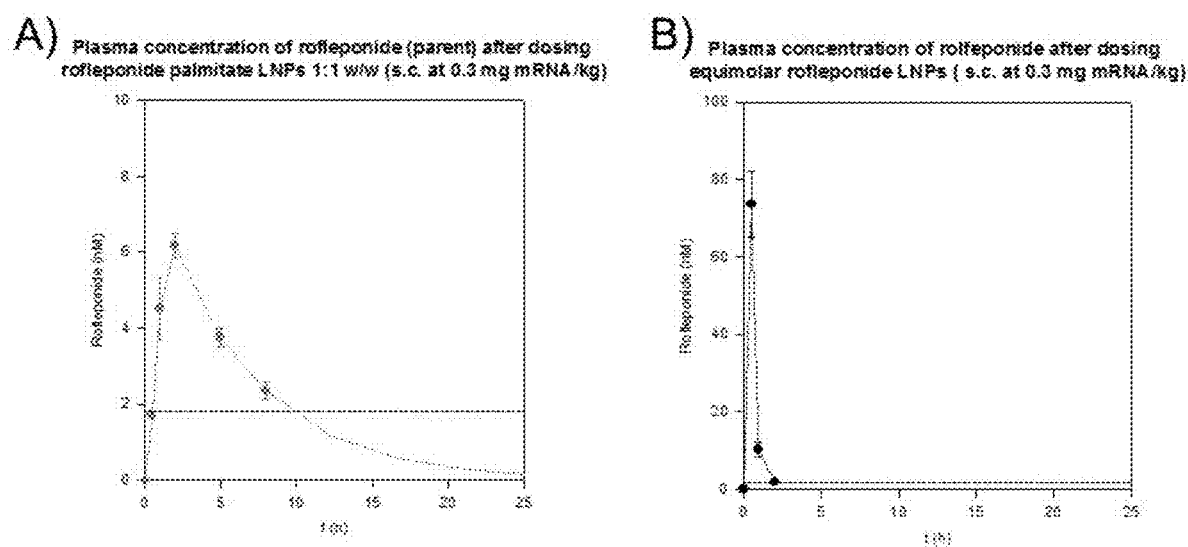
FIG. 5 illustrates rofleponide plasma concentration vs time after subcutaneous administration of LNPs containing rofleponide palmitate (R-C16, figure A) or rofleponide (figure B).
Figure 10A:
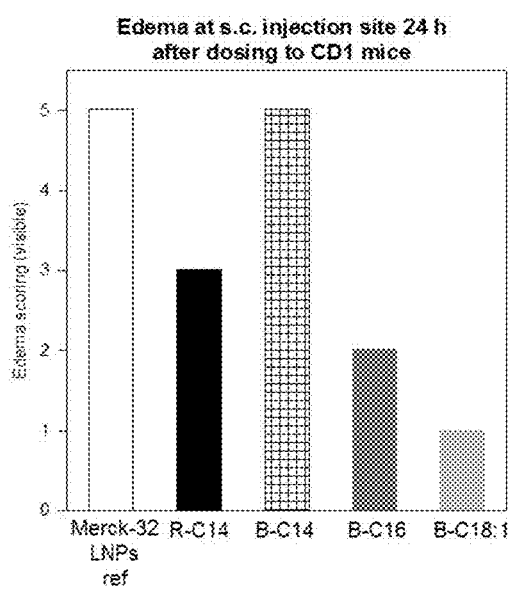
FIGS. 10A-G illustrate (A): edema scoring; (B): plasma haptoglobin concentration at 24 hours after administration; (C): plasma IL-6 concentrations at 7 and 24 hours post administration; (D): plasma KC concentrations at 7 and 24 hours post administration; (E) plasma IP-10 concentrations at 7 and 24 hours post administration; (F): plasma MCP-1 concentrations at 7 and 24 hours post administration; (G) mRNA 1 protein concentrations vs time after subcutaneous administration of LNPs containing budesonide pro-drugs with different fatty acid chain lengths: budesonide myristate (C14), budesonide palmitate (C16) or budesonide oleate (C18:1).
Figure 10B:
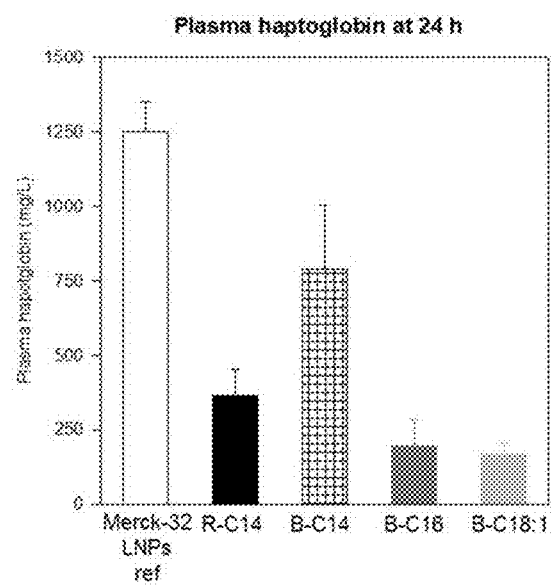
Figure 10C:
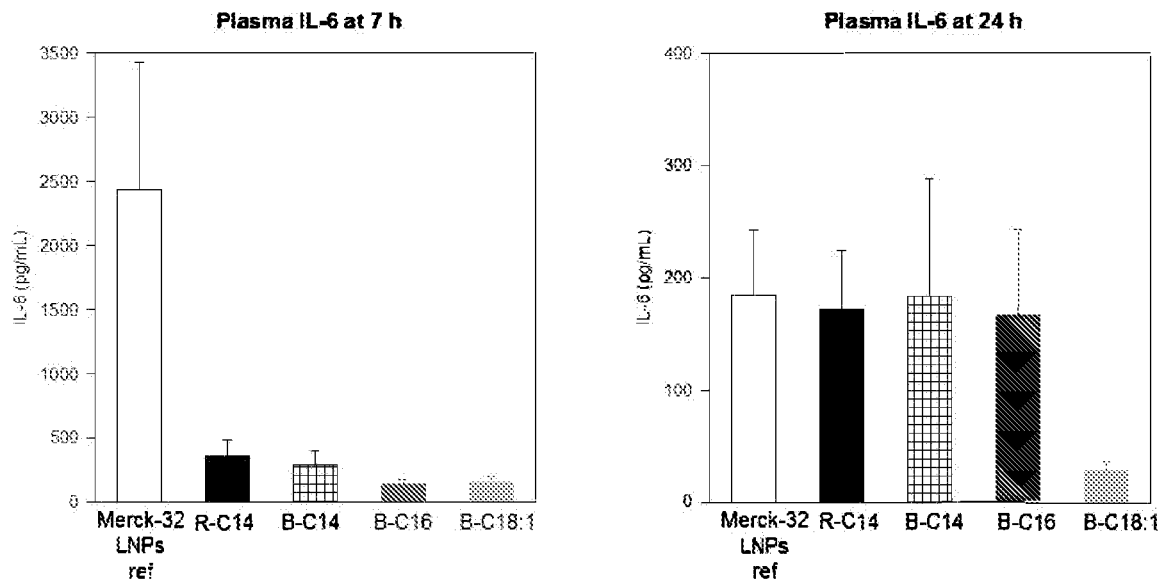
Figure 10D:
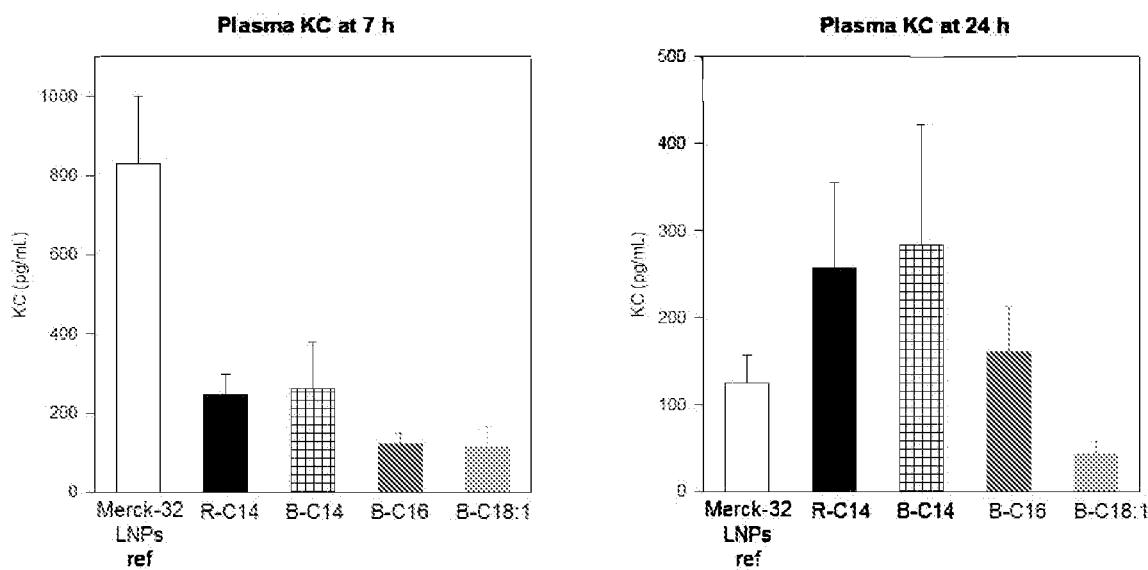
Figure 10E:
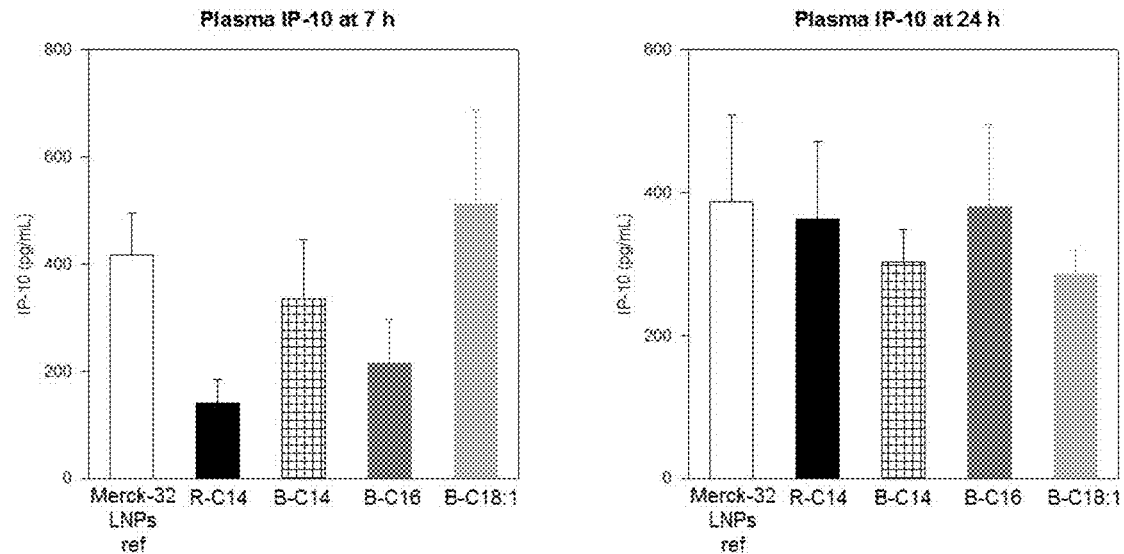
Figure 10F:
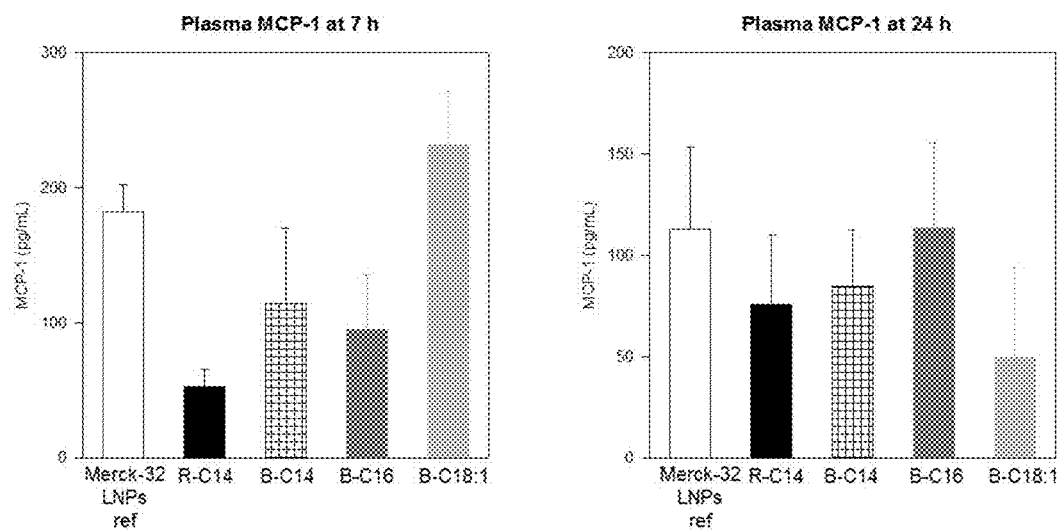
Figure 10G:
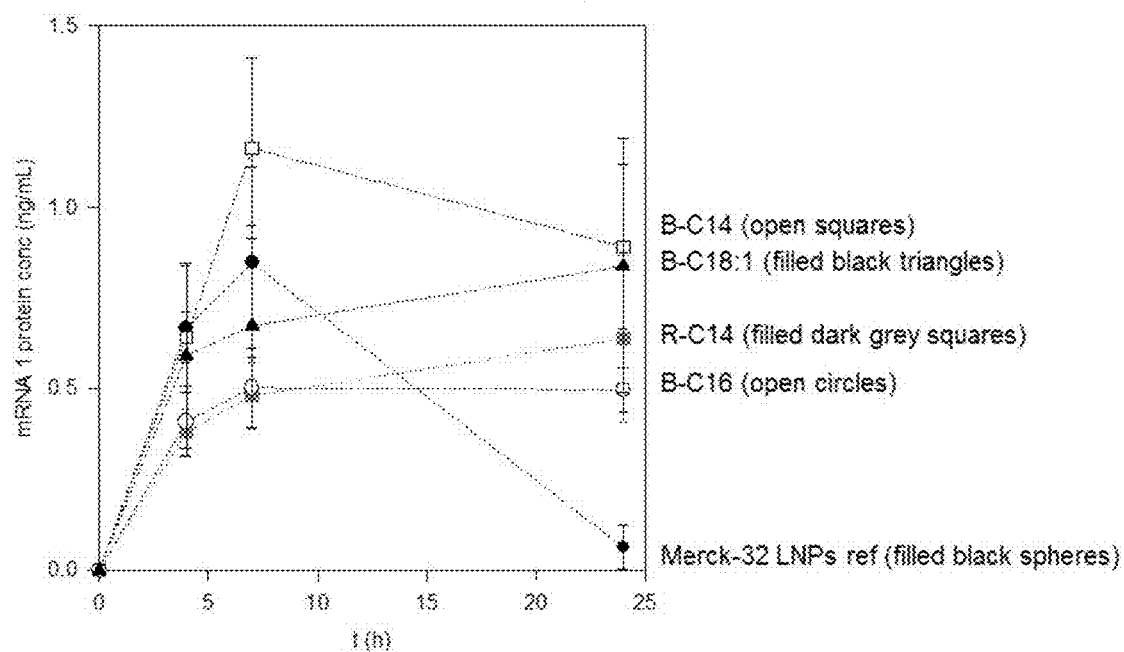

Samples S9 and S10 (see above) were administered subcutaneously to mice (N=16) at a dose of 0.3 mg mRNA/kg as described above. The results obtained for rofleponide plasma concentration vs. time are shown in FIG. 5. The results show a conversion of rofleponide palmitate to rofleponide after s.c. administration to mice of rofleponide palmitate LNPs. Furthermore, the results also clearly illustrate that the rofleponide LNPs gives rise to significantly higher initial plasma concentrations vs when rofleponide palmitate LNPs are used. This indicates that a significant portion of rofleponide is located in the cell versus the plasma with administration of LNPs comprising rofleponide palmitate as compared with LNPs with rofleponide mother compound, where a significant amount of rofleponide leaks into the plasma from the site of administration. Thus, the LNPs according to the present disclosure result in a total increase of therapeutic window, allowing for significantly smaller doses to be administered to the subject in need.

TABLE 4

Final molar compositions, measured particle sizes and % EE of samples S9 and S10.

| Sample | Composition [mol %] | Pre-dialysis Size [nm] | PDI | Postdialysis Size [nm] | PDI | % EE |
|---|---|---|---|---|---|---|
| S9 | MC3:DSPC:Cholesterol:DMPE-PEG2000:R-C16 46.29:9.20:35.61:1.48:7.42 | 92 | 0.04 | 86 | 0.08 | 98 |
| S10 | MC3:DSPC:Cholesterol:DMPE-PEG2000:rofleponide 46.29:9.20:35.61:1.48:7.42 | — | — | 91 | 0.12 | 98 |

Example 6: LNPs with Rofleponide Valerate, Rofleponide Myristate, Rofleponide Palmitate or Rofleponide Stearate The molar composition of the lipids used to prepare the lipid solution was DLin-MC3-DMA:DSPC:Cholesterol:DMPE-PEG2000=50:10:38.5:1.5. In addition the solution also contained rofleponide valerate (R-C5, sample S12), rofleponide myristate (R-C14, sample S13), rofleponide palmitate (R-C16, sample S14) or rofleponide stearate (R-C18, sample S15) at an amount which resulted in a total concentration of R-CX=0.25 mM in the pre dialysis LNP solution (where X=number of carbons in the chain). The final molar composition of the four lipids and R-CX in the LNPs are shown in Table 6 below. 2.475 mL of mRNA 1 solution and 0.825 mL of lipid and R-CX solution was mixed according the general description. The measured pre- and post-dialysis particle sizes as well the % EE are presented in Table 6 below (for the size measurement PBS, pH 7.4, was used).

TABLE 6

Final molar compositions, measured particle sizes and % EE of samples S11-S15.

| | | pre-dialysis | | post-dialysis | | |
|---|---|---|---|---|---|---|
| Sample | Composition [mol %] | Size [nm] | PDI | Size [nm] | PDI | % EE |
| S11 | MC3:DSPC:Cholesterol:DMPE-PEG2000 50:10:38.5.1.5 | 99 | 0.08 | 96 | 0.12 | 96 |
| S12 | MC3:DSPC:Cholesterol:DMPE-PEG2000:R-C5 46.29:9.20:35.61:1.48:7.42 | 110 | 0.07 | 101 | 0.09 | 95 |
| S13 | MC3:DSPC:Cholesterol:DMPE-PEG2000:R-C14 46.29:9.20:35.61:1.48:7.42 | 94 | 0.04 | 93 | 0.09 | 96 |
| S14 | MC3:DSPC:Cholesterol:DMPE-PEG2000:R-C16 46.29:9.20:35.61:1.48:7.42 | 95 | 0.04 | 93 | 0.09 | 95 |
| S15 | MC3:DSPC:Cholesterol:DMPE-PEG2000:R-C18 46.29:9.20:35.61:1.48:7.42 | 85 | 0.1 | 86 | 0.13 | 96 |

Phosphate buffer (PBS) and samples S11-S15 were administered subcutaneously to different groups of mice (N=5) at a dose of 0.3 mg mRNA/kg as described above. The results obtained for edema scoring, plasma haptoglobin, and plasma protein concentrations are shown in FIGS. 6A-C. The results show that by using R-C14, R-C16 or R-C18 LNPs according to the present disclosure, inflammation measured as edema scoring and haptoglobin is significantly reduced vs. non-anti-inflammatory LNPs, although inflammation was not significantly influenced using rofleponide valerate (R-C5). In addition, the R-C14, R-C16 or R-C18 LNPs give rise to an increased and prolonged protein expression vs. non-anti-inflammatory LNPs, although R-C5 LNPs did not produce a significantly increased total protein expression (0-24 h).

Example 7: LNPs with Merck-32 with and without Rofleponide Palmitate

Two samples were prepared (S16 and S17), in both samples the molar composition of the lipids used to prepare the lipid solution was Merck-32:DSPC:Cholesterol:DMPE-PEG2000=50:10:38.5:1.5. In addition, the solution used for S16 also contained rofleponide palmitate (R-C16) at an amount which resulted in a total concentration of R-C16=0.14 mM in the pre-dialysis LNP solution. The final molar composition of the four lipids and R-C16 in the LNPs are stated in Table 7 below. For S16, 2.925 mL of mRNA 1 solution and 0.975 mL of lipid and R-C16 solution was mixed and for S17, 0.75 mL of mRNA 1 solution and 0.25 mL of lipid and R-C16 solution was mixed according to the description above. For both S16 and S17, the molar ratio of ionizable lipid (Merck-32) and mRNA nucleotide was 6.0. The measured pre- and post-dialysis particle sizes as well the % EE are presented in Table 7 below (for the size measurement PBS, pH 7.4, was used).

TABLE 7

Final molar compositions, measured particle sizes and % EE of samples S16 and S17.

| | | Pre-dialysis | | Post-dialysis | | |
|---|---|---|---|---|---|---|
| Sample | Composition [mol %] | Size [nm] | PDI | Size [nm] | PDI | % EE |
| S16 | Merck-32:DSPC:Cholesterol:DMPE-PEG2000 50:10:38.5:1.5 | 99 | 0.15 | 94 | 0.14 | 98 |
| S17 | Merck-32:DSPC:Cholesterol:DMPE-PEG2000:R-C16 47.85:9.51:36.81:1.54:4.29 | 82 | 0.22 | 87 | 0.11 | 97 |

Phosphate buffer (PBS), samples S11 and S14 containing DLin-MC3-DMA (see Table 6) and samples S16-S17 containing Merck-32 were administered subcutaneously to different groups of mice (N=5) at a dose of 0.3 mg mRNA/kg as described above. The results obtained for edema scoring, plasma haptoglobin, and plasma protein concentrations are shown in FIGS. 7A-C. The results show that by using rofleponide palmitate in both DLin-MC3-DMA or Merck-32 based LNPs, inflammation measured as edema scoring and haptoglobin is significantly reduced. In addition, the presence of rofleponide palmitate in both DLin-MC3-DMA or Merck-32 based LNPs, give rise to an increased expression of mRNA 1 protein.

Example 8: LNPs with Merck-32 with Rofleponide Myristate (at Rolfeponide Myristate/mRNA Ratios 1:1 and 0.3:1 w/w) at a Higher mRNA Dose Three samples were prepared (S18-S20), the molar composition of the lipids used to prepare the lipid solution is stated in Table 8 below. For samples S19 and S20, the lipid mixture comprised MC3, DSPC, Cholesterol and PEG-lipid, and rofleponide myristate (R-C14) at an amount which resulted in a total concentration of R-C14=0.083 mM (S19) or 0.25 mM (SC20) in the pre-dialysis LNP solution. All samples were mixed according to the general description above. For sample S18, the volume of mRNA 1 solution was 2.13 mL and the volume of the lipid solution was 0.71 mL. For sample S19, the volume of mRNA 1 solution was 3.12 mL and the volume of the lipid and R-C14 solution was 1.04 mL. Sample S20 was composed of two batches identical batches where, for each batch, the volume of the mRNA 1 solution was 3.21 mL and the volume of the lipid and R-C14 solution was 1.07 mL. Both samples S19 and S20 were concentrated using Amicon Ultra-15 Centrifugal Filters to reach a concentration desired for dosing in vivo. Prior to the concentration step, the two batches making up sample S20 were mixed together. The measured pre- and post-dialysis particle sizes as well the % EE are presented in Table 8 below (for the size measurement PBS, pH 7.4, was used).

Phosphate buffer (PBS), samples S18 containing DLin-MC3-DMA and samples S20 containing Merck-32 and rofleponide myristate were administered subcutaneously to different groups of mice (N=5) at a dose of 0.3 mg mRNA/kg as described above. Furthermore, samples S19-S20 were also administered subcutaneously to groups of mice (N=5) at a higher mRNA dose, 1 mg/kg. The results obtained for edema scoring, plasma haptoglobin and plasma mRNA1 protein concentrations are shown in FIGS. 8A-C. The results show that by using rofleponide myristate in Merck-32 based LNPs at a R-C14/mRNA ratio of 1:1, inflammation measured as edema scoring at both 0.3 and 1 mg/kg, is reduced. In addition, protein expression shows approximate dose proportional increase (over the time interval 0-24 h) when comparing 0.3 and 1 mg/kg doses.

Example 9: LNPs with KL10 and Acuitas-5 with and without Rofleponide Myristate (at Rolfeponide Myristate/mRNA Ratios 1:1 w/w)

The molar composition of the lipids used to prepare the lipid solution is stated in Table 9 below. For samples S23 and S25, the lipid mixture contained, in addition to the ionizable lipid, DSPC, Cholesterol and PEG-lipid, rofleponide myristate (R-C14) at an amount which resulted in a total concentration of R-C14=0.28 mM (S23) or 0.17 mM (S25) in the pre dialysis LNP solution. All samples were mixed according to the general description with the exception that N:P=3 for samples S22 and S23 and N:P=4.9 for samples S24 and S25. For sample S21, the volume of mRNA 1 solution was 2.16 mL and the volume of the lipid solution was 0.72 mL. For sample S22 and S23, the volume of mRNA 1 protein solution was 1.41 mL and the volume of the lipid and R-C14 solution was 0.47 mL, and for sample S24 and S25, the volume of mRNA 1 protein solution was 1.77 mL and the volume of the lipid and R-C14 solution was 0.59 mL. The measured pre- and post-dialysis particle sizes as well the % EE are presented in Table 8 below (for the size measurement PBS, pH 7.4, was used).

TABLE 8

The final molar compositions, measured particle sizes and % EE of samples S18-S20. The two values for pre- and post-dialysis size and PDI for sample S20 represent the two different batches used to prepare the sample.

| Sample | Composition [mol %] | pre-dialysis | | post-dialysis | | | post-concentration | | |
|---|---|---|---|---|---|---|---|---|---|
| | | Size [nm] | PDI | Size [nm] | PDI | % EE | Size [nm] | PDI | % EE |
| S18 | MC3:DSPC:Cholesterol:DMPE-PEG2000 50:10:38.5.1.5 | 76 | 0.04 | 73 | 0.03 | 98 | — | — | — |
| S19 | Merck-32: DSPC:Cholesterol:DMPE-PEG2000:R-C14 49.3:9.8:37.92:1.58:1.4 | 67 | 0.06 | 72 | 0.17 | — | 67 | 0.08 | 98 |
| S20 | Merck-32:DSPC:Cholesterol:DMPE-PEG2000:R-C14 47.86:9.51:36.82:1.53:4.27 | 72/ 67 | 0.02/ 0.05 | 76/ 76 | 0.14/ 0.19 | — | 71 | 0.07 | 97 |

TABLE 9

The final molar compositions, measured particle sizes and % EE of samples S21-S25.

| | | pre-dialysis | | post-dialysis | | |
|---|---|---|---|---|---|---|
| Sample | Composition [mol %] | Size [nm] | PDI | Size [nm] | PDI | % EE |
| S21 | MC3:DSPC:Cholesterol:DMPE-PEG2000 50:10:38.5:1.5 | 78 | 0.02 | 79 | 0.05 | 97 |
| S22 | Acuitas-5:DSPC:Cholesterol:DMPE-PEG2000 50:10:38.5:1.5 | 64 | 0.03 | 77 | 0.05 | 97 |
| S23 | Acuitas-5: DSPC:Cholesterol:DMPE-PEG2000:R-C14 45.89:9.18:35.33:1.38:8.22 | 65 | 0.03 | 72 | 0.03 | 97 |
| S24 | KL10:DSPC:Cholesterol:DMPE-PEG2000 50:10:38.5:1.5 | 70 | 0.04 | 103 | 0.09 | 96 |
| S25 | KL10:DSPC:Cholesterol:DMPE-PEG2000:R-C14 47.41:9.42:36.47:1.52:5.18 | 77 | 0.05 | 122 | 0.08 | 93 |

Phosphate buffer (PBS), sample S21 containing DLin-MC3-DMA, samples S22-23 containing Acuitas-5 without and with rofleponide myristate (R-C14) and samples S24-25 containing KL10 without and with rofleponide myristate (R-C14), were administered subcutaneously to different groups of mice (N=5) at a dose of 0.3 mg mRNA/kg as described above. The results obtained for edema scoring, plasma haptoglobin and plasma mRNA 1 protein concentrations are shown in FIGS. 9A-C. The results show that by using rofleponide myristate in in both Acuitas-5 and KL10 based LNPs, inflammation measured as edema scoring and plasma haptoglobin is reduced compared to LNPs based on DLin-MC3-DMA (at 0.3 mg/kg). In addition, the mRNA 1 protein expression (over the time interval 0-24 h) is increased when rolfeponide myristate was incorporated into the LNPs.

Example 10: LNPs with Merck-32 Alone and with Rofleponide Myristate, Budesonide Myristate, Budesonide Palmitate or Budesonide Oleate The molar composition of the lipids used to prepare the lipid solution was L608:DSPC:Cholesterol:DMPE-PEG2000=50:10:38.5:1.5 (sample S26). Sample S27 also contained rofleponide myristate (R-C14) and for sample S29, S30, and S31, the solution also contained budesonide myristate (B-C14), budesonide palmitate (B-C16) and budesonide oleate (B-C18:1) respectively at an amount which resulted in a total concentration of R-C14, B-C14, B-C16 and B-C18:1=0.154 mM in the pre-dialysis LNP solution. The final molar composition of the four lipids and R-C14, B-C14, B-C16 or B-C18:1 in the LNPs are stated in Table 10 below. A 3.36 mL aliquot of mRNA 1 protein solution and 1.12 mL of lipid and R-C14, B-C14, B-C16 or B-C18:1 solution was mixed according to the general description described above under the "Preparation of LNPs containing mRNA," section described above. All the samples were concentrated using Amicon Ultra-4 Centrifugal Filters which were then spun at 3000 rpm and 8° C. until the formulations had an estimated mRNA concentration significantly higher than 0.2 mg/mL. The remaining formulation volumes were collected and the centrifugation filters were washed with small aliquots of PBS buffer which were added to the main sample fractions to give an estimated mRNA concentration around 0.2 mg/mL. Afterwards the size was measured again. The measured pre dialysis and post concentration particle sizes as well the % EE are presented in Table 10 below.

TABLE 10

The final molar compositions, measured particle sizes and % EE of samples S26-S31.

| | | Pre dialysis | | Post concentration | | |
|---|---|---|---|---|---|---|
| Sample | Composition [mol %] | Size [nm] | PDI | Size [nm] | PDI | % EE |
| S26 | L608:DSPC:Cholesterol:DMPE-PEG2000 50:10:38.5:1.5 | 72 | 0.07 | 74 | 0.09 | 97 |
| S27 | L608:DSPC:Cholesterol:DMPE-PEG2000:R-C14 49.77:9.89:38.09:1.48:1.06 | 75 | 0.05 | 78 | 0.08 | 97 |
| S29 | L608:DSPC:Cholesterol:DMPE-PEG2000:B-C14 49.77:9.89:38.09:1.48:1.06 | 78 | 0.06 | 79 | 0.10 | 93 |
| S30 | L608:DSPC:Cholesterol:DMPE-PEG2000:B-C16 49.77:9.89:38.09:1.48:1.06 | 75 | 0.08 | 78 | 0.10 | 97 |
| S31 | L608:DSPC:Cholesterol:DMPE-PEG2000:B-C18:1 49.77:9.89:38.09:1.48:1.06 | 75 | 0.11 | 78 | 0.11 | 97 |

Samples S26-S31 were administered subcutaneously to different groups of mice (N=5) at a dose of 0.3 mg mRNA/kg as described above. The results obtained for edema scoring, plasma haptoglobin, plasma cytokines/chemokines and plasma mRNA 1 concentrations are shown in FIGS. 10A-G. The results indicate that rofleponide myristate (R-C14), budesonide palmitate (B-C16) or budesonide oleate (B-C18:1) LNPs significantly reduce inflammation measured as edema scoring, haptoglobin and cytokines IL-6 and KC vs. conventional LNPs (Sample S26). Furthermore, inflammation was not influenced to the same extent when using Budesonide myristate (B-C14). In addition, the R-C14, B-C16 or B-C18:1 LNPs resulted in an increased and prolonged expression of mRNA 1 vs. conventional LNPs (Sample S26).

What is claimed is:

1. An anti-inflammatory lipid nanoparticle comprising:
   a) a lipid phase, wherein the lipid phase comprises at least one ionizable lipid, at least one neutral lipid, at least one sterol, and at least one polymer-conjugated lipid;
   wherein the at least one ionizable lipid is chosen from DLin-MC3-DMA, Merck 32, KL10, Acuitas 5, and mixtures thereof
   the at least one neutral lipid is distearoyl phosphatidylcholine (DSPC);
   the at least one sterol is cholesterol; and
   the at least one polymer-conjugated lipid is at least one pegylated lipid; and
   b) at least one lipophilic anti-inflammatory agent, wherein the lipophilic anti-inflammatory agent is chosen from rofleponide valerate (C5), rofleponide caproate (C6), rofleponide caprylate (C8), rofleponide caprate (C10), rofleponide laurate (C12), rofleponide myristate (C14), rofleponide palmitate (C16), rofleponide stearate (C18), budesonide myristate (C14), budesonide palmitate (C16), budesonide stearate (C18), budesonide oleate (C18:1), and budesonide linoleate (C18:2); and
   c) an mRNA;
   wherein the anti-inflammatory lipid nanoparticle does not have a continuous aqueous region exceeding 50% by volume.

2. The anti-inflammatory lipid nanoparticle according to claim 1, wherein the at least one ionizable lipid is DLin-MC3-DMA.

3. The anti-inflammatory lipid nanoparticle according to claim 1, wherein the at least one polymer-conjugated lipid is chosen from DMPE-PEG2000, DPPE-PEG2000, DMG-PEG2000, DPG-PEG2000, PEG2000-c-DOMG, PEG2000-c-DOPG, and mixtures thereof.

4. The anti-inflammatory lipid nanoparticle according to claim 1, wherein the lipophilic anti-inflammatory agent is chosen from rofleponide valerate (C5), rofleponide caproate (C6), rofleponide caprylate (C8), rofleponide caprate (C10), rofleponide laurate (C12), rofleponide myristate (C14), rofleponide palmitate (C16), or rofleponide stearate (C18).

5. The anti-inflammatory lipid nanoparticle according to claim 1, wherein the lipophilic anti-inflammatory agent is chosen from budesonide myristate (C14), budesonide palmitate (C16), budesonide stearate (C18), budesonide oleate (C18:1), and budesonide linoleate (C18:2).

6. The anti-inflammatory lipid nanoparticle according to claim 4, wherein the weight ratio of lipid phase to mRNA ranges from about 40:1 to 1:1.

7. The anti-inflammatory lipid nanoparticle according to claim 1, wherein the weight ratio of lipophilic anti-inflammatory agent to mRNA ranges from about 10:1 to about 1:100.

8. A pharmaceutical composition comprising a plurality of anti-inflammatory lipid nanoparticles according to claim 1.

\* \* \* \* \*